US009539152B2

(12) United States Patent
Suzuki et al.

(10) Patent No.: US 9,539,152 B2
(45) Date of Patent: Jan. 10, 2017

(54) ABSORBENT ARTICLE WITH NEW LEG GATHERS

(75) Inventors: Migaku Suzuki, Tokyo (JP); Yoshio Hirai, Tokyo (JP)

(73) Assignee: DAIO PAPER CORPORATION, Shikokuchuo (JP)

(*) Notice: Subject to any disclaimer, the term of this patent is extended or adjusted under 35 U.S.C. 154(b) by 186 days.

(21) Appl. No.: 14/378,192

(22) PCT Filed: Feb. 14, 2012

(86) PCT No.: PCT/JP2012/053402
§ 371 (c)(1),
(2), (4) Date: Aug. 12, 2014

(87) PCT Pub. No.: WO2013/121528
PCT Pub. Date: Aug. 22, 2013

(65) Prior Publication Data
US 2015/0080828 A1    Mar. 19, 2015

(51) Int. Cl.
*A61F 13/49* (2006.01)
*A61F 13/494* (2006.01)

(52) U.S. Cl.
CPC ..... *A61F 13/49007* (2013.01); *A61F 13/4942* (2013.01); *A61F 2013/49063* (2013.01);
(Continued)

(58) Field of Classification Search
CPC .......................... A61F 13/475; A61F 13/4752;
A61F 13/4753; A61F 13/494; A61F
13/49406; A61F 13/49413; A61F
13/4942; A61F 2013/4944; A61F
2013/49493
See application file for complete search history.

(56) References Cited

U.S. PATENT DOCUMENTS 5,167,653 A * 12/1992 Igaue .................. A61F 13/4942
604/385.04
5,674,213 A * 10/1997 Sauer .................. A61F 13/4942
604/378
(Continued)

FOREIGN PATENT DOCUMENTS

FR   EP 1166729 A1 *  1/2002  ....... A61F 13/49413
JP   U-5-48922          6/1993
(Continued)

OTHER PUBLICATIONS

International Search Report issued in International Application No. PCT/JP2012/053402 mailed May 1, 2012.
(Continued)

*Primary Examiner* — Lynne Anderson
*Assistant Examiner* — Kathryn E Ditmer
(74) *Attorney, Agent, or Firm* — Oliff PLC

(57) ABSTRACT

An absorbent article has: a leak preventer sheet form; an absorber arranged above the leak preventer and absorbs bodily fluid in at least one layer; and a pair of right and left floating leg gathers arranged, above the absorber, from front end to rear end part in length direction of the absorbent article via a front body, a crotch part and rear body. Floating leg gathers have head and hanging parts connecting to the head parts, respectively. A front end and a rear end parts of each of the hanging parts respectively coupled near a front end part and rear end part of the body of the absorbent article, each hanging part hangs down from the head part toward the absorber; hanging parts of floating leg gathers fixed to the absorber at a lower end part of the hanging part in the crotch part without fixing to the absorber.

14 Claims, 12 Drawing Sheets

(52) U.S. Cl.
CPC ............... *A61F 2013/49092* (2013.01); *A61F 2013/49493* (2013.01)

(56) References Cited

U.S. PATENT DOCUMENTS

| | | | |
|---|---|---|---|
| 6,692,475 B2* | 2/2004 | Mishima | A61F 13/495 |
| | | | 604/385.19 |
| 6,767,343 B2* | 7/2004 | Shimada | A61F 13/496 |
| | | | 604/385.25 |
| 2002/0058920 A1* | 5/2002 | Toyoda | A61F 13/49011 |
| | | | 604/385.28 |
| 2002/0138060 A1* | 9/2002 | Nakaoka | A61F 13/505 |
| | | | 604/385.25 |
| 2004/0181202 A1* | 9/2004 | Corneliusson | A61F 13/49413 |
| | | | 604/385.27 |
| 2006/0135930 A1* | 6/2006 | Mizutani | A61F 13/47218 |
| | | | 604/385.17 |
| 2006/0135931 A1* | 6/2006 | Suzuki | A61F 13/495 |
| | | | 604/385.19 |
| 2009/0005752 A1* | 1/2009 | Suzuki | A61F 13/494 |
| | | | 604/385.101 |
| 2010/0057033 A1 | 3/2010 | Kurihara | |
| 2012/0095425 A1 | 4/2012 | Nishitani et al. | |

FOREIGN PATENT DOCUMENTS

| | | |
|---|---|---|
| JP | A-2004-24310 | 1/2004 |
| JP | A-2004-89271 | 3/2004 |
| JP | A-2007-236911 | 9/2007 |
| JP | A-2008-161255 | 7/2008 |
| JP | A-2010-187919 | 9/2010 |
| JP | A-2010-246614 | 11/2010 |
| JP | A-2011-194152 | 10/2011 |
| KR | 2002-0069174 A | 8/2002 |

OTHER PUBLICATIONS

Apr. 24, 2012 Office Action issued in Japanese Application No. 2012-513396 (with translation).

May 1, 2012 Written Opinion issued in International Application No. PCT/JP2012/053402 (with translation).

* cited by examiner

A

B

ABSORBENT ARTICLE WITH NEW LEG GATHERS

FIELD OF THE INVENTION

The present invention relates to an absorbent article.

BACKGROUND ART

An object of absorbent articles, exemplified by infant's paper diapers, adult's paper diapers and sanitary napkins, is to prevent leakage of mainly bodily fluids such as urine and feces or the like, from the sides (side leakage) of the absorbent articles, and the absorbent articles are provided with leg gathers as indispensable structural components thereof.

Leg gathers are generally classified into two types. One type is an outer leg gather (also referred to as a "gusset gather." Hereinafter, an outer leg gather will be referred to as an "OLG") which is present on both the right and left side edges of the absorbent article body. The other is an inner leg gather (hereinafter, referred to as an "ILG") which is provided inside the absorbent article and which sterically rises from both right and left sides of an absorber which is configured from a super absorbent polymer, pulp or the like.

Of these leg gathers, the ILG fulfills two functions in that, when the bodily fluid is excreted from a wearer, such bodily fluid that flows over the absorber surface is blocked by the side faces and at the same time the bodily fluid is prevented from transferring along the skin and leaking to the outside by allowing an end part (head part) of the ILG to make contact with the wearer's skin.

In order to fulfil such functions, ILGs conventionally have the following configurations:

(i) A leg part that blocks the bodily fluid on the side face and a head part that is connected from the leg part and that prevents the transfer and leakage by allowing the head part to make contact with the wearer's skin, are provided;

(ii) The head part is made of a stretchable material which allows it to have adhesion with the wearer's skin;

(iii) The leg part is configured by making use of a hydrophobic non-woven fabric which has leakage prevention properties for the material for preventing the permeation of bodily fluids.

(iv) The leg part is bonded to the absorber surface or the surface of a top sheet that covers the absorber surface and is configured to rise therefrom by using the bonded parts as a base end part; and (v) The base end part of the leg part is bonded to near the right and left side edge parts of the absorber (or to the top sheet parts corresponding to the positions of the right and left side edge parts).

Such conventional absorbent articles, at the time of use, absorb the bodily fluid excreted onto an absorber, which is present between the right and left ILGs, in a manner of pressing and adhering such absorber against/to the wearer's skin.

However, in the absorbent articles having such conventional ILGs, the absorber and the ILGs, which are coupled thereto and are stiff, are pressed into a narrow crotch part and thus, irregular deformations such as kinks and folds or the like easily occur in the absorber, the absorption of bodily fluids is concentrated to part of the absorber and leakage easily occurs. In addition, an exchange to a new absorbent article is performed due to the generation of a feeling of discomfort arising from the above situation, and also, when used for an infant's diaper, due to the change of color of the so-called "pee indicator" prior to absorbing a predetermined amount of urine. Such pee indicator indicates the timing for changing diapers by, for example, changing the color when a predetermined amount of urine is excreted. Thus, currently, the absorbent articles having such conventional ILGs are not used according to the absorption capacity of the absorber. In fact, according to the statistics, in the case of current diapers for infants, the average value of the absorbed amount of bodily fluids in the absorbent article at the time of changing to an unused absorbent article is 50% or less of the absorption capability of the absorber.

Moreover, as described above, since, at the time of use of the absorbent article, the absorbent, which is present between the right and left ILGs, is pressed against and adhered to the wearer's skin, the urine and feces excreted onto the absorber will make contact with the wearer's skin for a prolonged period of time and skin troubles, such as diaper rash or the like, will be caused.

In order to solve such problems of conventional ILGs, it has been proposed to prevent kinks and folds or the like in the absorber by providing OLGs as well as by bringing the bonding positions of the ILGs to the absorber closer to the middle in the lateral direction (See Patent Document 1).

PRIOR ART REFERENCES

Patent Documents

Patent Document 1: Japanese Laid-Open Utility Model Application No. H05-048922

SUMMARY OF THE INVENTION

Problems Solved by the Invention

However, according to the inventors' consideration, the disposable diaper described in Patent Document 1 does not differ from the absorbent article having the conventional ILGs with respect to the point that the absorber is pressed against and adhered to the wearer's skin at the time of use of the absorbent article and thus, the problems to the effect that the urine and feces excreted onto the absorber come into contact with the wearer's skin and that thus skin troubles, such as diaper rash or the like, may be caused, are not solved.

The object of the present invention is to provide an absorbent article, in which the contact of urine and feces excreted onto an absorber with a wearer's skin, at the time of use of an absorbent article, is effective suppressed.

Means for Solving the Problems

As result of diligently conducting research so as achieve the object set forth above, the present inventors have found that: by providing, as a pair of right and left floating leg gathers (hereinafter also referred to as "FLG") arranged, above an absorber, from a front end part to a rear end part in the length direction of the absorbent article body via a front body, a crotch part and a rear body, the FLG which has a head part and a hanging part that connects to the head part, a front end part and a rear end part of the hanging part respectively being coupled near to a front end part and near to a rear end part of the absorbent article body, and the hanging part being configured to hang down from the head part toward the absorber; by allowing the hanging part of the FLG to not be fixed to the absorber in the front body and the rear body and a lower end part of the hanging part to be fixed to the absorber in the crotch part; and by allowing, at the time of use, the head part of the FLG to make contact with a wearer's skin and a spaced-apart condition with respect to the absorber to be maintained, the FLGs are spaced apart from the absorber at the time of use of the absorbent article and thus, the contact of urine or feces excreted onto the absorber with the wearer's skin is effectively suppressed, and then completed the present invention.

Namely, the present invention provides the following (1) to (15):

(1) An absorbent article, including:
a leak preventer in sheet form;
an absorber that is arranged above the leak preventer and is capable of absorbing a bodily fluid in at least one layer; and
a pair of right and left floating leg gathers that are arranged, above the absorber, from a front end part to a rear end part in a length direction of a body of the absorbent article via a front body, a crotch part and a rear body,
wherein the floating leg gathers have head parts and hanging parts that connect to the head parts, respectively, a front end part and a rear end part of each of the hanging parts respectively being coupled near to a front end part and near to a rear end part of the body of the absorbent article, and each of the hanging parts hangs down from the head part toward the absorber,
wherein the hanging parts of the floating leg gathers are fixed to the absorber at a lower end part of the hanging part in the crotch part, without fixing to the absorber in the front body and the rear body, and
wherein, at a time of use, the head parts of the floating leg gathers make contact with a wearer's skin and maintains a spaced-apart condition with respect to the absorber.

(2) The absorbent article according to section (1), wherein the pair of right and left floating leg gathers are arranged such that both head parts face outward and both hanging parts face inward and such that the lower end parts of the hanging parts are opposed to each other near the middle in a width direction of the absorber. (3) The absorbent article according to section (1) or (2), wherein
the pair of right and left floating leg gathers are arranged such that a spaced-apart distance between the hanging parts is narrow at the crotch part and widens from the crotch part toward each of the front end part and the rear end part.

(4) The absorbent article according to section (1) or (2), wherein
the pair of right and left floating leg gathers are arranged such that a spaced-apart distance between the hanging parts narrows down from the crotch part to the rear end part and widens from the crotch part toward the front end part.

(5) The absorbent article according to section (1) or (2), wherein
the pair of right and left floating leg gathers are arranged such that a spaced-apart distance between the hanging parts narrows down from the crotch part to the front end part and widens from the crotch part toward the rear end part.

(6) The absorbent article according to any one of sections (1) to (5), wherein
the minimum spaced-apart distance between the lower end parts of the hanging parts of the pair of right and left floating leg gathers is 40 mm or less.

(7) The absorbent article according to any one of sections (1) to (5), wherein
the pair of right and left floating leg gathers are arranged such that parts of the hanging parts overlap with each other in the crotch part.

(8) The absorbent article according to any one of sections (1) to (5), further comprising a coupling band that couples the hanging parts of the pair of right and left floating leg gathers to each other at the crotch part, and
by the coupling band being fixed to the absorber at the crotch part, the hanging part of the floating leg gather is indirectly fixed to the absorber.

(9) The absorbent article according to any one of sections (1) to (8), wherein
Each of the hanging parts of the floating leg gathers is fixed to the absorber, at a plurality of locations, in the crotch part.

(10) The absorbent article according to any one of sections (1) to (9), wherein
the hanging parts of the floating leg gathers have a cut line or a cutout.

(11) The absorbent article according to any one of sections (1) to (10), wherein
the head parts of the floating leg gathers have stretchability.

(12) The absorbent article according to section (11), wherein
each of the floating leg gathers is formed by coupling a belt-like Stretchable body to a sheet-like member in an extended condition, the belt-like Stretchable body configuring the head part, the sheet-like member configuring the hanging part, and
the hanging part has folds.

(13) The absorbent article according to section (11) or (12), wherein
the coupling is respectively performed between the front end part and the rear end part of the hanging part of each of the floating leg gather and near the front end part and near the rear end part of the body of the absorbent article, in a condition in which the floating leg gathers are stretched in a front-rear direction.

(14) The absorbent article according to any one of sections (1) to (13), further comprising a pair of right and left inner leg gathers provided further outside from the positions where the pair of left and right floating leg gathers are present in the width direction.

(15) The absorbent article according to any one of sections (1) to (14), further comprising a pair of right and left outer leg gathers provided further outside from the positions where the pair of left and right floating leg gathers are present in the width direction.

Effect of the Invention

In the absorbent article according to the present invention, the contact of urine and feces excreted onto the absorber with a wearer's skin, at the time of use of the absorbent article, is effectively suppressed.

BRIEF DESCRIPTIONS OF THE DRAWINGS

Figure 6:
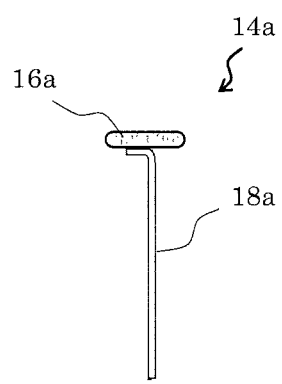
Figure 6:
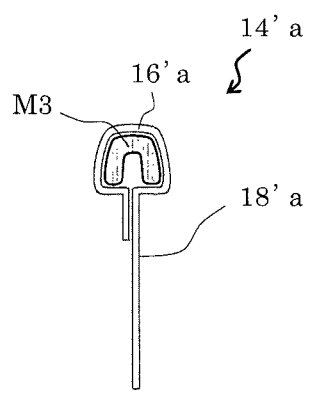
Figure 6:
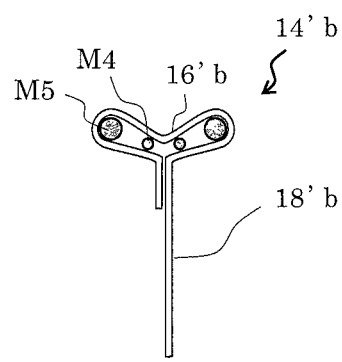
Figure 6:
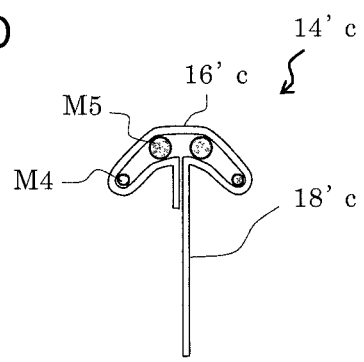
Figure 6:
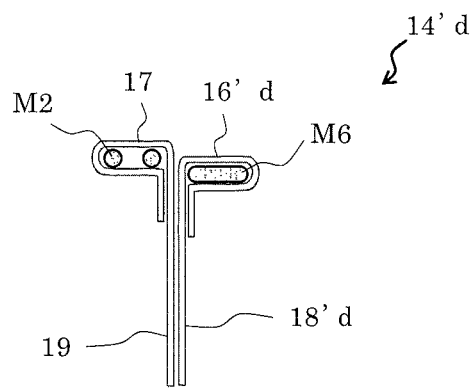

FIG. 6 contains schematic lateral end face views illustrating FLGs having head parts with various shapes.

Figure 7:
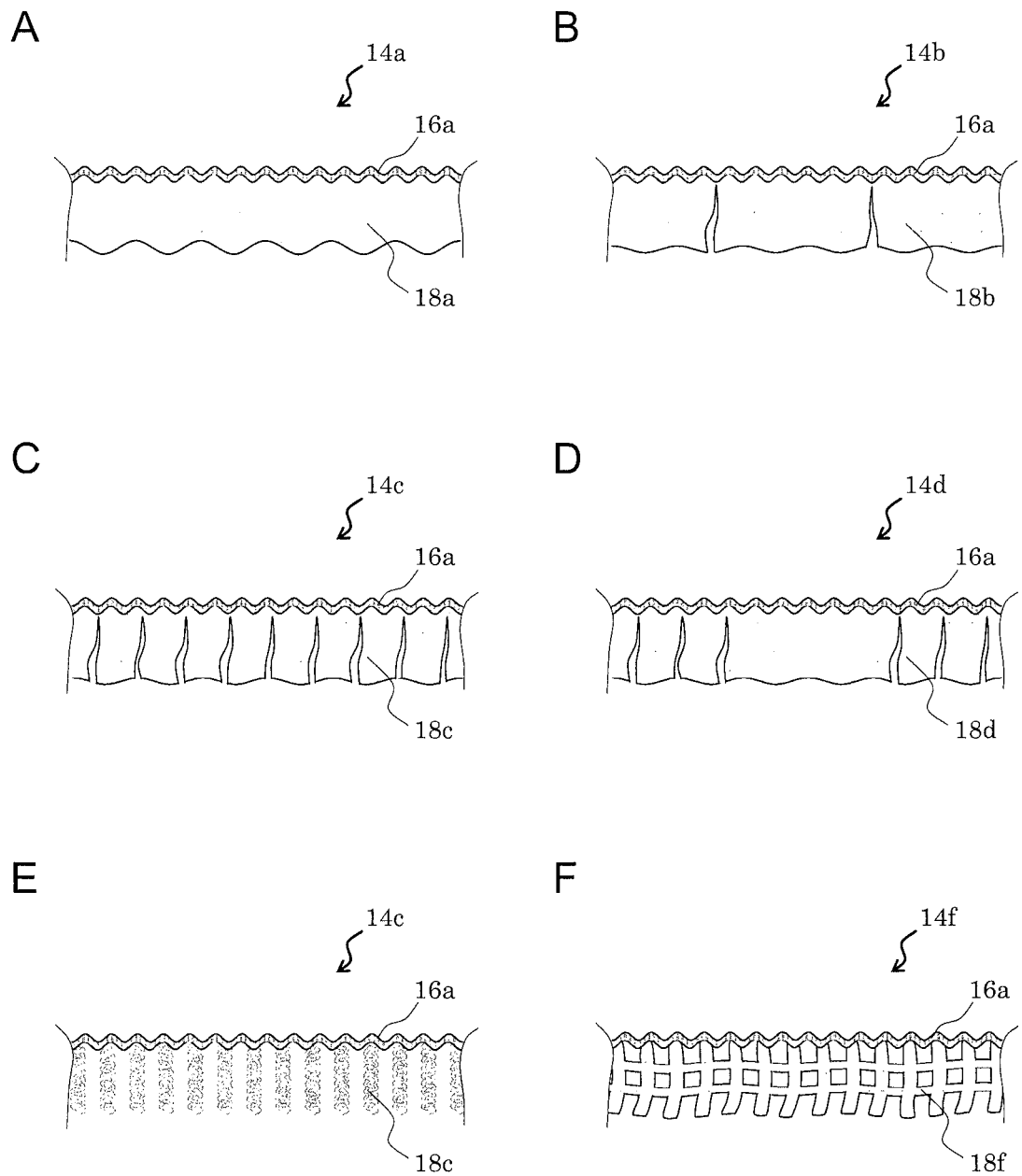

FIG. 7 contains schematic partial side views illustrating FLGs having hanging parts with various shapes.

Figure 8:
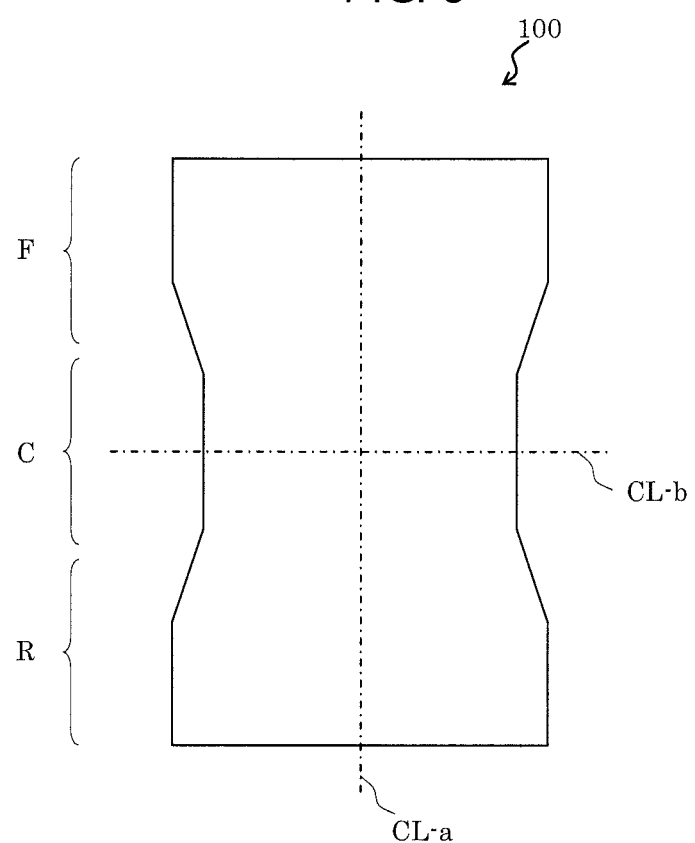

FIG. 8 is a schematic plan view of an absorbent article according to the present invention.

Figure 9:
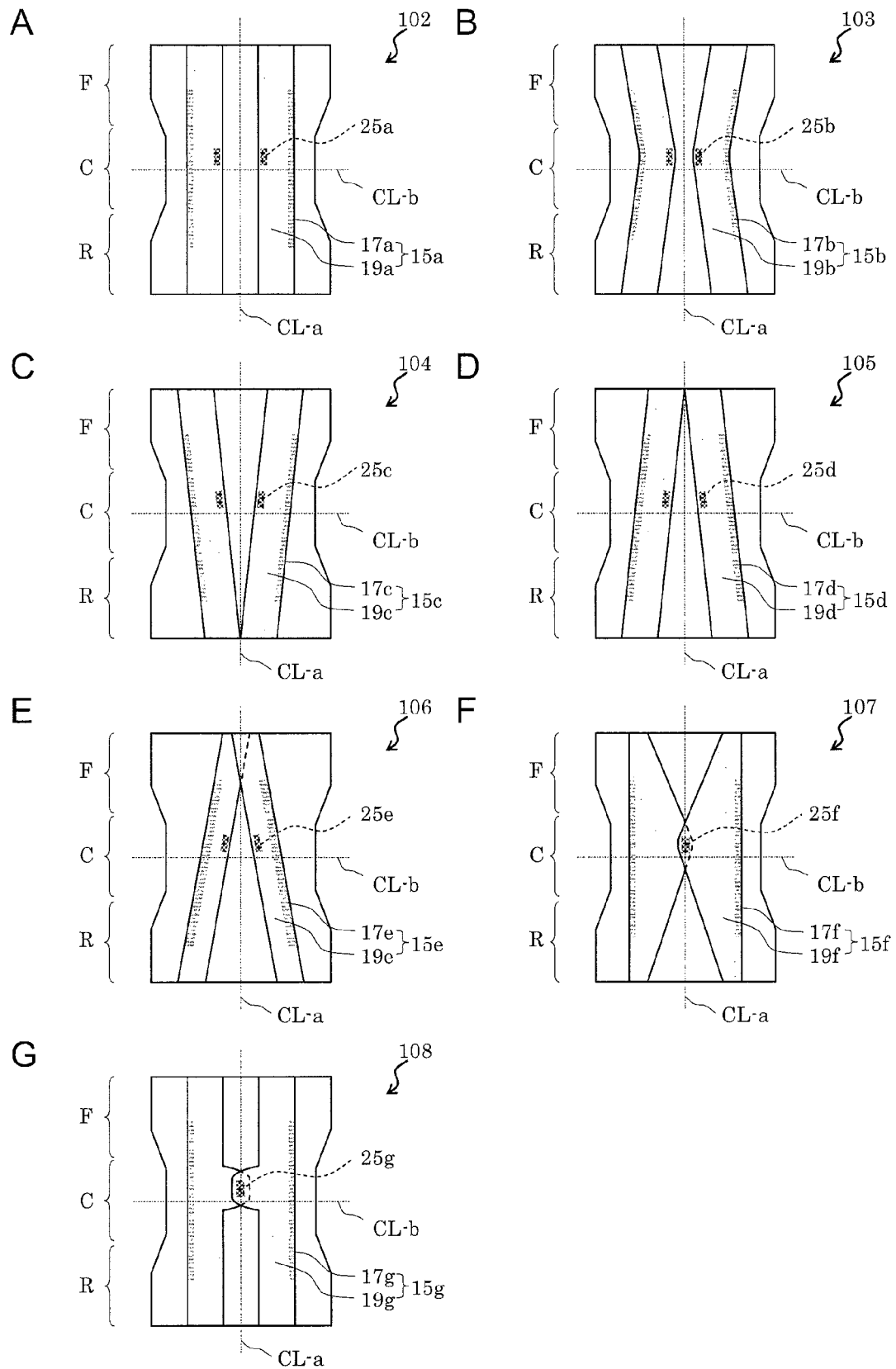

FIG. 9 contains schematic plan views of the absorbent articles with FLGs in various arrangement embodiments.

Figure 10:
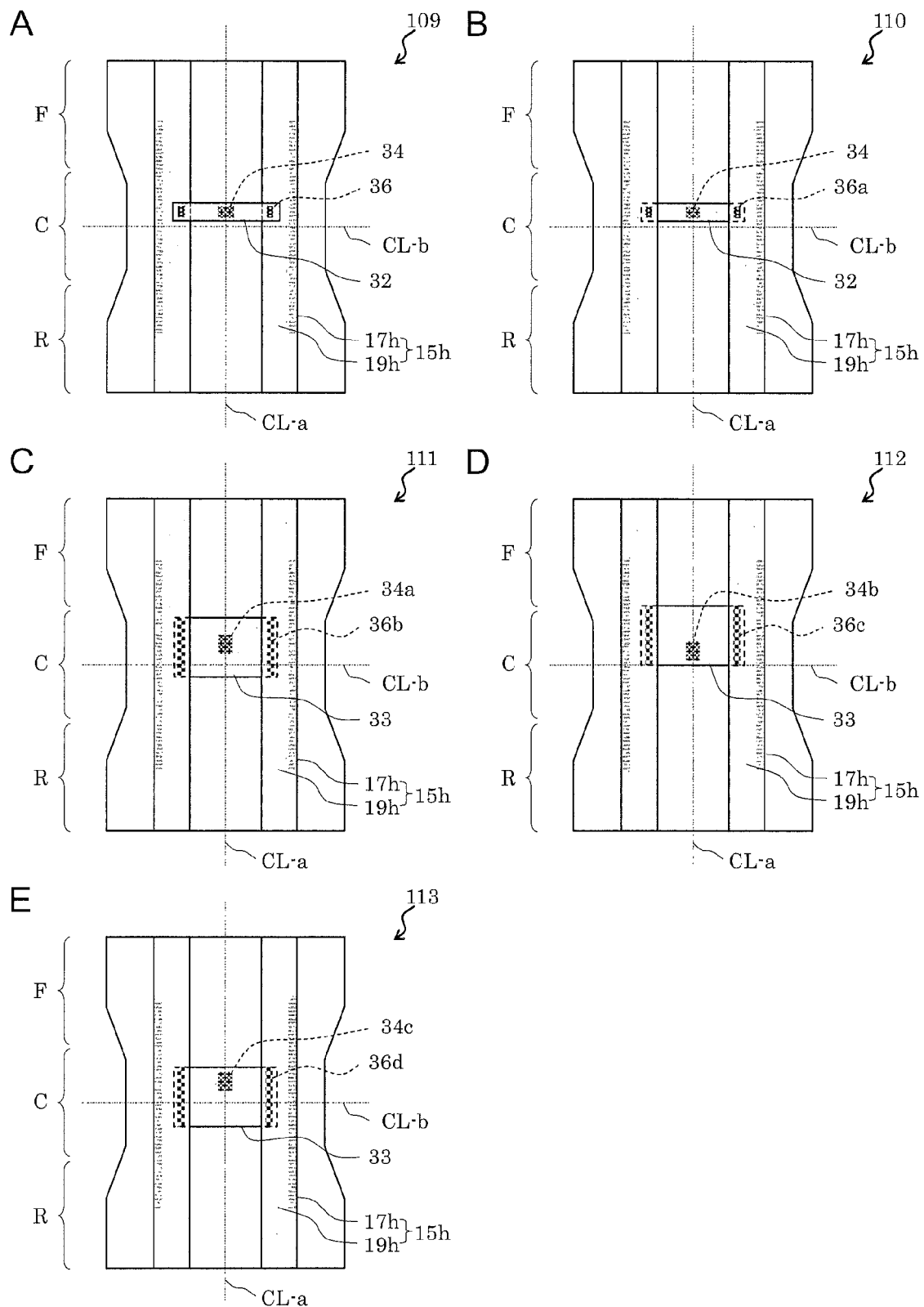

FIG. 10 contains schematic plan views of the absorbent articles with FLGs in various arrangement embodiments.

Figure 11:
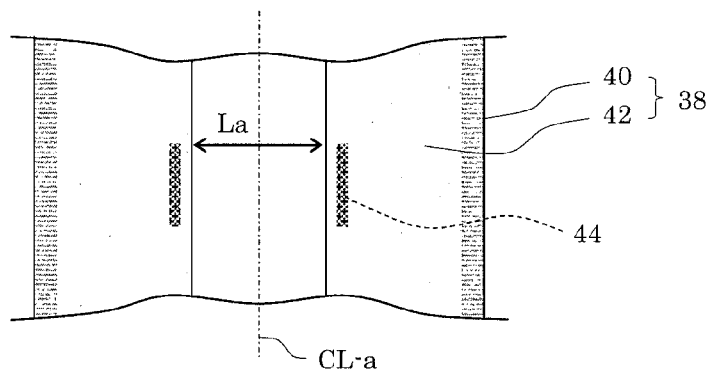
Figure 11:
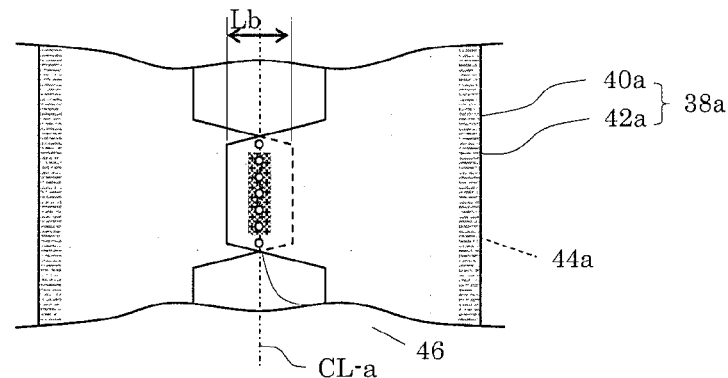
Figure 11:
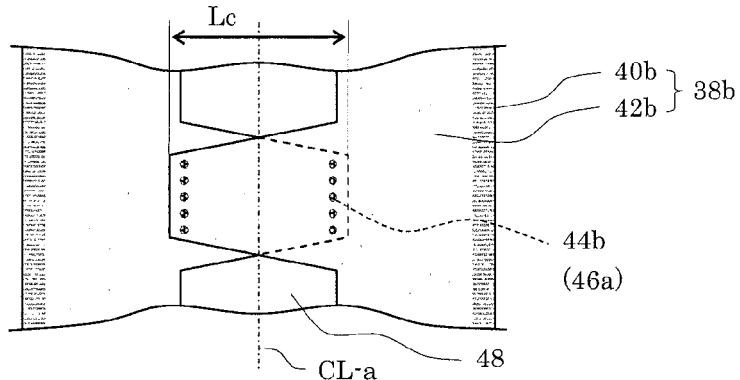
Figure 11:
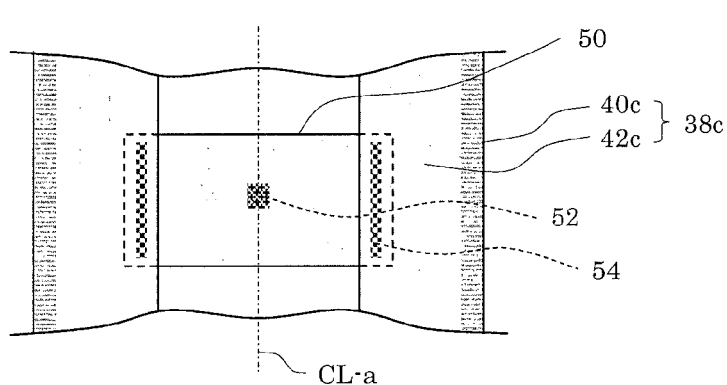

FIG. 11 contains views for describing the fixing condition between the hanging parts of the FLGs and the absorber.

Figure 12:
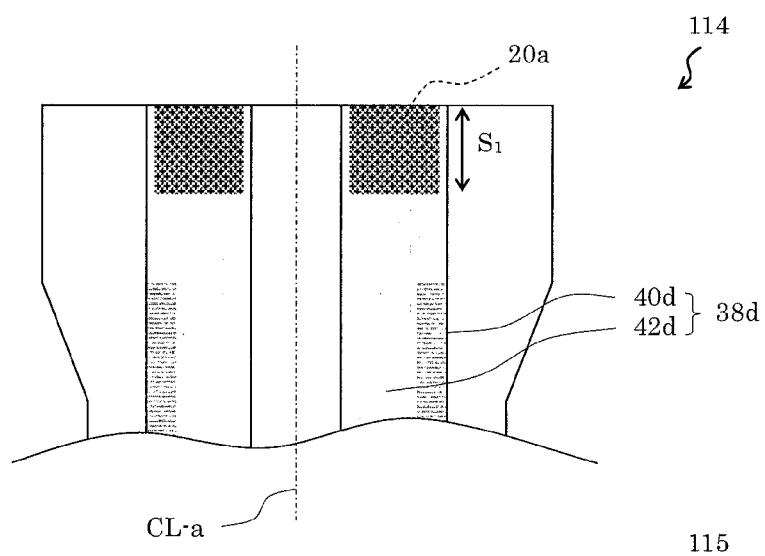
Figure 12:
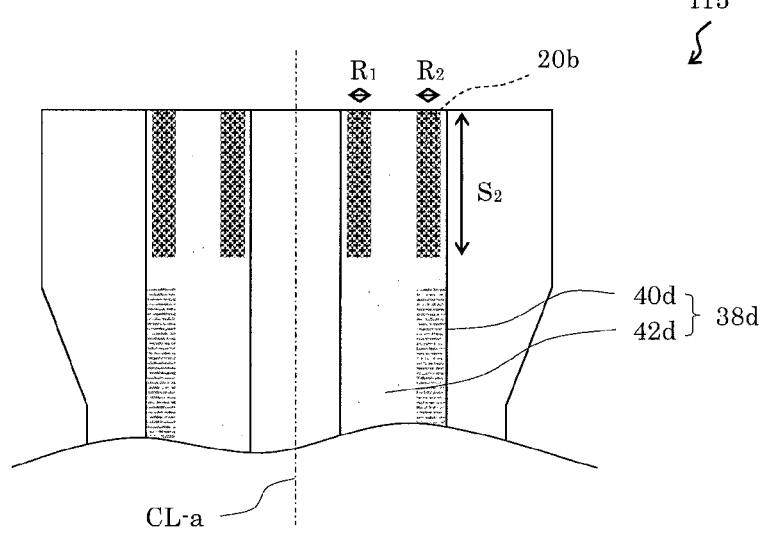
Figure 12:
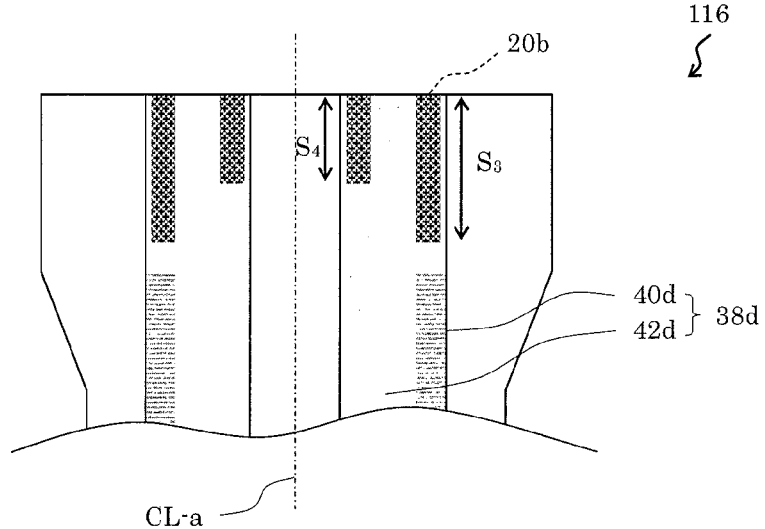

FIG. 12 contains views for describing the fixing condition when arranging an FLG to the absorbent article body.

EMBODIMENTS OF THE INVENTION

Hereinafter, the absorbent article according to the present invention will be described in detail, based on the preferred embodiments illustrated in the attached drawings. It should be noted that, in the present specification, when the absorbent article according to the present invention is actually worn, a side close to the skin of the wearer will be referred to as the "top" and, a side far therefrom will be referred to as the "bottom/under." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. Moreover, in order to facilitate understanding, in the respective drawings, members that are actually in contact with each other may be illustrated such that they are spaced apart. In the respective plan views among the attached FIGS. 1, 3 and 5, the front side of the absorbent article, etc. is illustrated such that it is positioned on the left side of the corresponding drawing, and in the other respective plan views, the front side of the absorbent article, etc. is illustrated such that it is positioned on the top side of the corresponding drawing. In the respective longitudinal end face views and longitudinal sectional views among the attached drawings, the front side of the absorbent article, etc. is illustrated such that it is positioned on the left side of the corresponding drawing.

Figure 1:
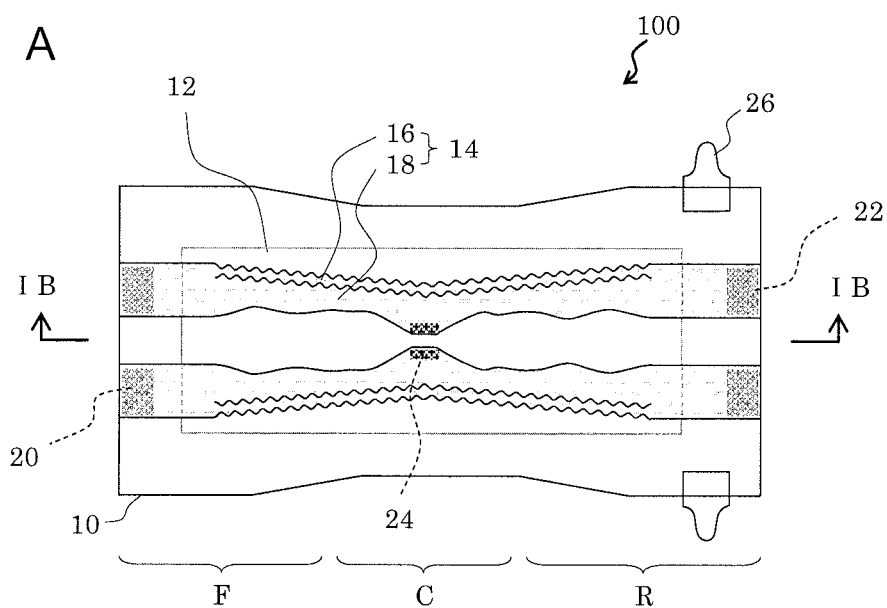
FIG. 1 is a schematic diagram illustrating an example of an absorbent article according to the present invention.
Figure 1:
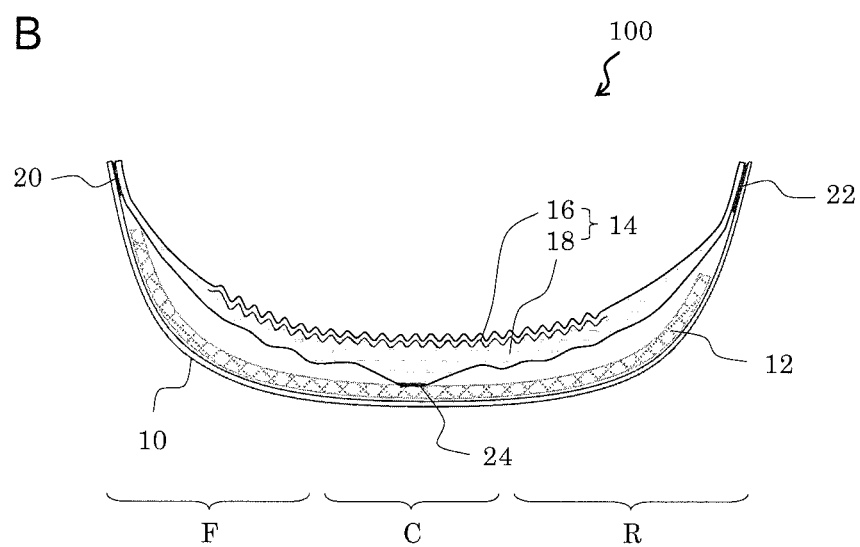

FIG. 1 is a schematic diagram illustrating an example of an absorbent article according to the present invention. FIG. 1(A) is a plan view thereof and FIG. 1(B) is a longitudinal sectional view taken along line IB-IB shown in FIG. 1(A).

Absorbent article 100 according to the present invention illustrated in FIG. 1 is configured as an infant's diaper and basically includes: leak preventer 10 in sheet form; absorber 12 capable of absorbing a bodily fluid, wherein at least one layer thereof is arranged above leak preventer 10; and a pair of right and left FLGs 14 arranged, above absorber 12, from a front end part to a rear end part in the length direction of the absorbent article body via a front body, a crotch part and a rear body. It should be noted that the dimensions of the various members of the absorbent article are described herein by assuming an infant's diaper.

Materials that are generally used as a back sheet can be used for the materials of leak preventer 10. In particular, a resin film made of, for example, PE, PP, PET, EVA or the like and a bodily fluid impermeable sheet such as a foam sheet made of the resin described above can be used. For the bodily fluid impermeable sheet, a sheet having air permeability, such as an air permeable sheet or the like may be preferably used.

In addition, when the above-described resin film is used, a multilayered sheet of such film and a non-woven fabric may be used in order to improve the texture and appearance. In this case, a spunbond (SB) or thermalbond non-woven fabric having a relatively low basis weight (for example, an air-through type) or the like may preferably be used as the non-woven fabric.

Moreover, a multilayered sheet of such resin film and an absorber in sheet form, which is described below, may also be used.

Further, a high water-resistance non-woven fabric may also be used. Examples of such high water-resistance non-woven fabric include an SMS non-woven fabric having a degree of water resistance of 100 mmH$_2$O or more and an SMS non-woven fabric in which pores in a web are filled with microfibrillated cellulose (MFC) or wax so as to provide such fabric with water resistance. In this case, a high water-resistance non-woven fabric may be used alone or may also be used as a multilayered sheet of the film and such high water-resistance non-woven fabric.

Leak preventer 10 may be configured from a plurality of members.

Leak preventer 10 is in sheet form; however, as long as it accommodates absorber 12 or the like above leak preventer 10 and is capable of being arranged with FLGs 14, the shape thereof is not particularly limited.

Absorber 12 used in the present invention is not particularly limited, as long as it is capable of absorbing bodily fluid, and any absorber used in publicly-known conventional absorbent articles may be used. For example, powdery wooden pulp, a powdery absorber (such as raw SAP, etc.) and an absorber in sheet form may be used.

An absorber in sheet form excels in morphological stability and capability of SAP fall prevention, etc.

Among various types of absorber in sheet form, a super absorbent sheet containing 50 wt % or more, preferably 60 wt % or more, or more preferably 70 wt % or more of SAP is preferred. In addition, from the perspective of stability, etc. of the super absorbent sheet, the content of SAP therein is preferably 95 wt % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, crushed wooden pulp and SAP are mixed and a binder is added to shape the mixture into a sheet form and then a super absorbent sheet is obtained. As examples of a super absorbent sheet obtained through this process, NOVATHIN (US trademark) manufactured by Rayonier Inc. in the US and B-SAP manufactured by Oji Kinocloth Co., Ltd. are known.

Another example of the super absorbent sheet includes a super absorbent sheet obtained through a process involving coating a bodily fluid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (trademark) manufactured by Japan Absorber Technology Institute is known.

Other examples of the super absorbent sheet include: a super absorbent sheet obtained through a process involving having a raised non-woven fabric carry a large amount of SAP and fixing the SAP with a hot melt binder, an emulsion binder, a water soluble fiber, or the like; a super absorbent sheet obtained through a process involving mixing fiber state SAP with a PET (polyethylene terephthalate) fiber and forming the mixture into a web; and an SAP sheet obtained by providing tissues above and below an SAP layer.

At least one layer of absorber 12 is arranged above leak preventer 10. Namely, absorber 12 may be comprised of one layer or two or more layers (multilayer).

In addition, absorber 12 may be arranged in a folded condition.

A pair of right and left FLGs 14 are arranged above absorber 12 from a front end part to a rear end part in the length direction of absorbent article body 100 via front body F, crotch part C and rear body R.

Here, "the body of absorbent article" collectively refers to a leak preventer, which is a member of the absorbent article, a top sheet, which can be provided above the leak preventer, and various other members, which can be provided to the absorbent article. The FLGs may be provided by being coupled to the leak preventer, may be provided by being coupled to the top sheet provided above the leak preventer or to the other members, or may be provided by being coupled to a plurality of members.

FLG 14 has head part 16 and hanging part 18 that connects to head part 16, and a front end part and a rear end part of hanging part 18 are respectively coupled near to a front end part and near to a rear end part of absorbent article 100 body (in FIG. 1, front end coupling part 20 and rear end coupling part 22 are shown). Hanging part 18 is configured to hang down from head part 16 toward absorber 12. The coupling method is not particularly limited and, for example, the coupling method may be achieved with an adhesive.

As shown in FIG. 1(B), hanging part 18 hangs down in curtain form and it does not rise due to being coupled to, fixed to and supported by the absorber (or the top sheet covering the absorber) as in conventional ILGs. Hanging part 18 is basically not fixed to the absorber and floats from absorber 12. Since such new FLG 14 has a floating configuration as described above, it will herein be referred to as a "floating leg gather" (FLG). Such floating configuration may be achieved by making, for example, the length between front end coupling part 20 and rear end coupling part 22 in FLG 14 smaller than the length between front end coupling part 20 and rear end coupling part 22 in leak preventer 10.

Hanging part 18 of FLG 14 is not fixed to absorber 12 in front body F and rear body R and is spaced apart from the surface of absorber 12, and the lower end part thereof is fixed to absorber 12 at fixing part 24 for the hanging part in crotch part C. The fixing method is not particularly limited and, for example, the fixing method may be a method using an adhesive.

A pair of hanging part fixing parts 24 are positioned in the vicinity of the middle in the width direction at the crotch part. Accordingly, the lower end parts of hanging parts 18 of FLGs 14 are fixed to the surface of absorber 12 at crotch part C and FLGs 14 form a space separated by curtain-like hanging parts 18, each extending into front body F or rear body R from crotch part C.

In addition, at the time of use, head part 16 of FLG 14 makes contact with the wearer's skin; however, it maintains a spaced-apart condition with respect to absorber 12.

When the lower end parts of the hanging parts of the FLGs are fixed to the absorber at the positions in the vicinity of the middle in the width direction at the crotch part, the space between the hanging parts on both right and left sides serves as a receiving part for the bodily fluids in the crotch part. The bodily fluid excreted into such space directly moves over the surface of the absorber or flows downwards along the hanging parts and moves to the surface of the absorber. The bodily fluid collected in the vicinity of the middle in the width direction of the crotch part will further move forward or backward of the absorber, depending on the body position of the wearer. For example, in a side lying position, in conventional diapers, the bodily fluid transferred along the wearer's skin may flow out from a gap between the wearer's skin and the ILGs. Even when the bodily fluid is blocked by the ILGs, it will be collected at the side end parts of the absorber and leakage can easily occur from the diaper side parts. These issues constitute major disadvantages. In the case of the FLGs in the absorbent article according to the present invention, by allowing the bodily fluid: to be reliably blocked by the head parts and the hanging parts; to be transferred along the inner surfaces of the hanging parts; and to be reliably moved forward and backward, side leakage can be significantly reduced. As described above, in the absorbent article according to the present invention, since the bodily fluid excreted between the hanging parts on both the right and left sides is accumulated at the crotch part and is evenly distributed in the front-rear direction and the width direction, no phenomenon occurs that would lead to a leakage such as, as in conventional diapers, the bodily fluid moving forward or laterally bypassing, depending on the position where the excretory organ (in particular, the penis) makes contact with the absorber. As a result, the absorption capability of the absorber can be sufficiently fulfilled.

In addition, as in the pair of FLGs 14 illustrated in FIG. 1(A), when the spaced-apart distance between the hanging parts varies depending on the position in the length direction (for example, the spaced-apart distance between the hanging parts may be arranged such that it is narrow at the crotch part and widens from the crotch part toward each of the front end part and rear end part), the movement of the bodily fluid in the lateral direction also occurs, and thus, in both the length direction and width direction of absorber 12, the bodily fluid can be diffused over a wide area and then absorbed. Accordingly, the absorption capability of absorber 12 can be further fulfilled.

A preferable range of the minimum spaced-apart distance between the pair of hanging parts will be described below.

Moreover, when the lower end parts of the hanging parts of the FLGs are fixed to the absorber at the positions in the vicinity of the middle in the width direction in the crotch part, the wearer can easily wear the absorbent article according to the invention at the time of use, since the head parts of the FLGs easily fit to the perineal area of the crotch part.

In addition, since the head parts of the FLGs are constantly adhered to the wearer's skin, the bodily fluid excreted from the wearer is suppressed from moving to the outside by transferring along the wearer's skin, in the space between the FLGs.

Figure 2:
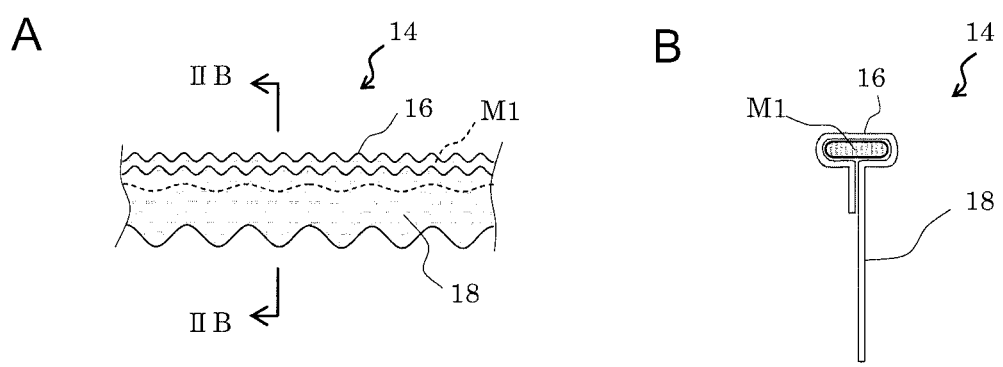
FIG. 2 is a partial schematic diagram of an FLG used in the absorbent article illustrated in FIG. 1.

FIG. 2 is a partial schematic diagram of FLG 14 used in absorbent article 100 illustrated in FIG. 1. FIG. 2(A) is a side view thereof and FIG. 2(B) is a cross sectional view taken along line IIB-IIB shown in FIG. 2(A).

As shown in FIG. 2, FLG 14 is configured from head part 16 and hanging part 18 that hangs down in a curtain form from head part 16. In particular, belt-like stretchable body M1, which extends in the length direction, is enclosed by a sheet-like member, and the excess part is made to hang down. Belt-like stretchable body M1 is covered with the sheet-like member to form head part 16, and hanging part 18 is formed from the hanging part of the sheet-like member.

Stretchable body M1 is not particularly limited and, for example, polyurethane foam (manufactured by, for example, Inoac Corporation) may be used.

The sheet-like member is not particularly limited and, for example, a PE/PP spunbond non-woven fabric (manufactured by, for example, JNC Corporation and having a basis weight of 15 g/m$^2$) and an SMS non-woven fabric may be used.

Since belt-like stretchable body M1 is used, head part 16 of FLG 14 has stretchability. When the head part of the FLG has stretchability, the degree of adhesion to the wearer's skin becomes high.

Detachable members 26 are provided on both the right and left sides in the vicinity of the rear end of leak preventer 10. On the under surface in the vicinity of the front end of leak preventer 10, a detachable member (not shown) are provided such that they can be detached from the detachable members. These detachable members may be configured by, for example, various hook-and-loop fasteners.

Figure 3:
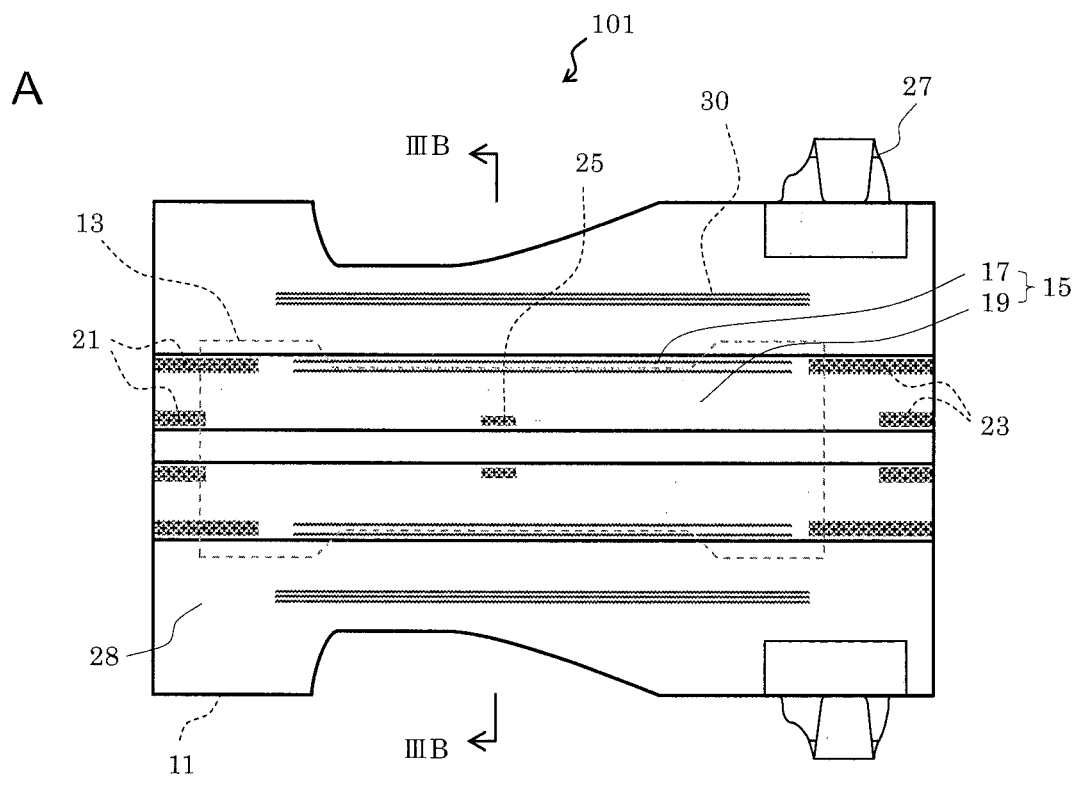
FIG. 3 is a schematic diagram illustrating another example of an absorbent article according to the present invention.
Figure 3:
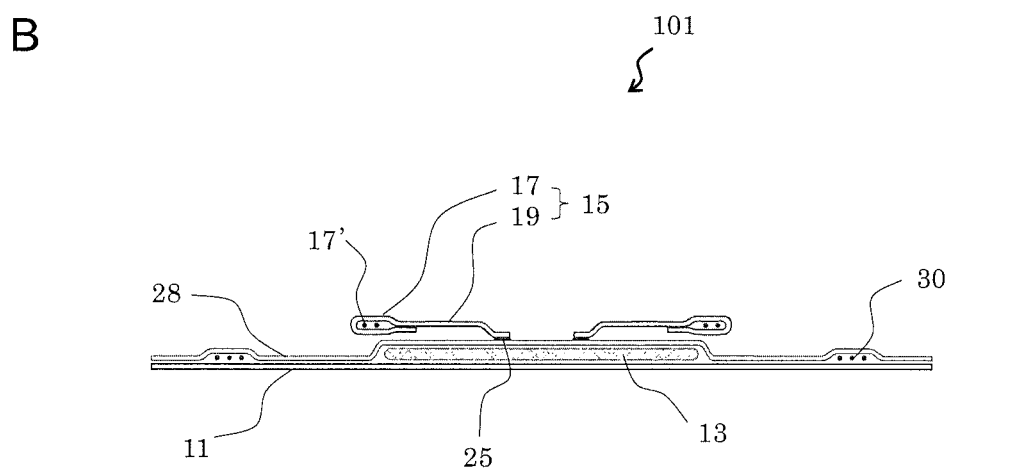

FIG. 3 is a schematic diagram illustrating another example of an absorbent article according to the present invention. FIG. 3(A) is a developed plan view in which stress is applied in order to stretch and develop the absorbent article in the front-rear direction and the lateral direction; and FIG. 3(B) is a lateral end face view taken along line IIIB-IIIB shown in FIG. 3(A).

Absorbent article 101 according to the present invention illustrated in FIG. 3 is configured as an infant's diaper and is basically similar to absorbent article absorbent article 100; however, it differs therefrom with respect to the point that a pair of right and left outer leg gathers are provided on the side parts outside the FLGs. Absorbent article 101 includes: leak preventer 11 in sheet form; absorber 13 capable of absorbing a bodily fluid, wherein at least one layer thereof is arranged above leak preventer 11; and a pair of right and left FLGs 15 arranged, above absorber 13 and near the middle in the width direction, from a front end part to a rear end part in the length direction of the absorbent article body via a front body, a crotch part and a rear body. However, it differs from absorbent article 100 with respect to the point that it further includes: top sheet 28 arranged so as to cover the surface of absorber 13 from one edge part in the width direction of leak preventer 11 to the other edge part thereof; and outer leg gathers arranged on both the right and left sides of absorber 13 above leak preventer 11 and are provided with pieces of yarn-like rubber 30 which are fixed by being covered with top sheet 28.

As for yarn-like rubber 30, for example, three polyurethane filaments may be used. Yarn-like rubber 30 configures, together with leak preventer 11 and top sheet 28 which sandwich and fix the yarn-like rubber from top and bottom, a pair of right and left OLGs outside the positions where the pair of right and left FLGs are present in the width direction.

According to the present invention, the configuration of the OLG is not limited to this configuration and, for example, a configuration of the OLG used in the conventionally and publicly-known absorbent articles may be used.

Leak preventer 11, absorber 13, FLG 15, head part 17, stretchable body M2, hanging part 19, front end coupling part 21, rear end coupling part 23, fixing part 25 for the hanging part and detachable member 27 in absorbent article 101, respectively correspond to leak preventer 10, absorber 12, FLG 14, head part 16, stretchable body M1, hanging part 18, front end coupling part 20, rear end coupling part 22, fixing part 24 for the hanging part and detachable member 26 in absorbent article 100, despite the fact that they differ with respect to details such as shape, etc. (it should be noted that, as shown in FIG. 3(A), each of front end coupling part 21 and rear end coupling part 23 has two positions, i.e. right and left positions).

Absorbent article 101 illustrated in FIG. 3 is in a condition where it is stretched and developed in the front-rear direction and the lateral direction by applying stress thereto.

In this developed condition, FLGs 15 are tensioned in the front-rear direction and lie flat above top sheet 28. As is clear from FIG. 3(B), in this condition, the lower ends of hanging parts 19 of FLGs 15 are fixed at a pair of hanging part fixing parts 25, present near the middle in the width direction, by being coupled to absorber 13 via top sheet 28, and head parts 17 are located outward from hanging part fixing parts 25. When the lower ends of the hanging parts are located on the inside and the head parts thereof are located on the outside, the required width between the hanging parts can be easily adjusted and the manufacturing process can also be simplified.

As is clear from FIG. 3(A), in the developed condition, although the lower ends of hanging parts 19 of the pair of right and left FLGs 15 are located such that they are opposed to each other, they are only coupled to absorber 13 at hanging part fixing parts 25 at the crotch part.

It should be noted that, in the present invention, in the case where the surface of the absorber is covered with a top sheet, an embodiment in which the hanging parts of the FLGs are fixed to the top sheet is also included in the embodiments in which the hanging parts of the FLGs are fixed to the absorber, since such hanging parts are indirectly fixed to the absorber via the top sheet.

Figure 4:
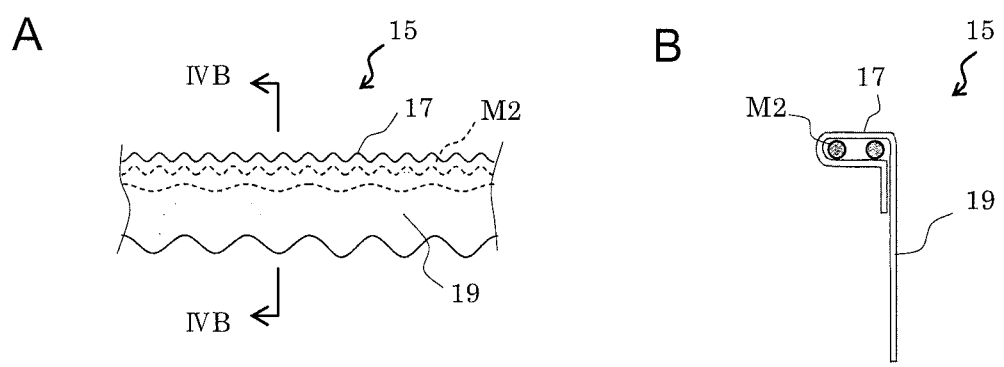
FIG. 4 is a partial schematic diagram of an FLG used in the absorbent article illustrated in FIG. 3.

FIG. 4 is a partial schematic diagram of FLG 15 used in absorbent article 101 illustrated in FIG. 3. FIG. 4(A) is a side view thereof and FIG. 4(B) is a cross sectional view taken along line IVB-IVB shown in FIG. 4(A).

As shown in FIG. 4, FLG 15 is configured from head part 17 and hanging part 19 that hangs down in a curtain form from head part 17. In particular, belt-like stretchable body M2, which extends in the length direction, is enclosed by a sheet-like member, and the excess part is made to hang down. Belt-like stretchable body M2 is covered with the sheet-like member to form head part 17, and hanging part 19 is formed from the hanging part of the sheet-like member.

Unlike stretchable body M1, stretchable body M2 that configures head part 17 of FLG 15 is configured by two pieces of yarn-like rubber or polyurethane filaments which lie parallel in the length direction.

Unlike hanging part 18 of FLG 14 which hangs down substantially from the middle in the width direction of head part 16, hanging part 19 of FLG 15 hangs down from the inner side edge in the width direction of head part 17 (FLG 15 shown in FIG. 4 is an FLG on the left hand side when seen from the wearer).

In absorbent article 101, when the stress is removed, FLGs 15 will float from the surface of absorber 13, similar to the case with absorbent article 100 shown in FIG. 1(B), due to the contraction of stretchable body M2 of head part 17.

Top sheet 28 is configured by a liquid permeable non-woven fabric (such as an air-through non-woven fabric (for example, with a basis weight of 20 g/m$^2$) made of PE/PET and which has been subjected to hydrophilization treatment).

In the present invention, the top sheet is not particularly limited and, for example, any top sheet used in conventionally and publicly-known absorbent articles may be used.

Figure 5:
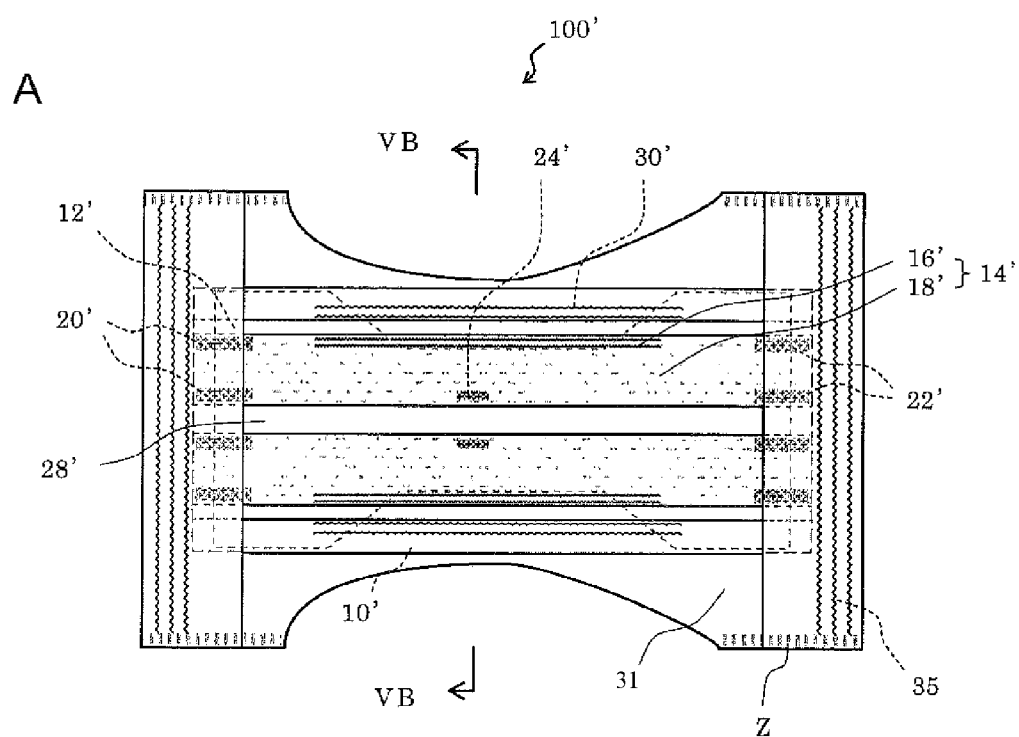
FIG. 5 is a schematic diagram illustrating yet another example of an absorbent article according to the present invention.
Figure 5:
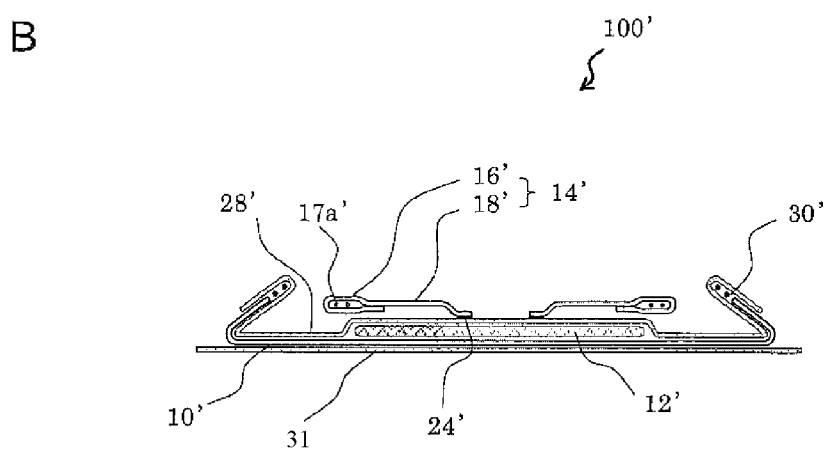

FIG. 5 is a schematic diagram illustrating yet another example of an absorbent article according to the present invention. FIG. 5(A) is a plan view of an absorbent article in the form of an underpants-type diaper, which is cut along the right and left side parts (denoted with "Z" in the figure) of the waist gather and developed; and FIG. 5(B) is a lateral end face view taken along line VB-VB shown in FIG. 5(A).

Absorbent article 100 shown in FIG. 1 and absorbent article 101 shown in FIG. 3 are both examples of a tape-type diaper for infants. However, absorbent article 100' shown in FIG. 5 is an example of a tapeless, underpants-type diaper.

Absorbent article 100' shown in FIG. 5 is basically similar to absorbent article 101 shown in FIG. 3; however it differs therefrom with respect to the points that it is an underpants-type diaper and that it further has a pair of right and left ILGs on the outer side of the positions in the width direction where a pair of right and left FLGs are present. Namely, absorbent article 101 illustrated in FIG. 3 represents a combination use example of the FLGs and OLGs, and absorbent article 100' illustrated in FIG. 5 represents a combination use example of the FLGs and ILGs.

It should be noted that, in the present invention, the combinations of FLGs with OLGs and ILGs are not particularly limited. For example, FLGs may be used alone (see absorbent article 100 shown in FIG. 1), or alternatively, any of a combination of FLGs and OLGs located outward thereof (see absorbent article 101 shown in FIG. 3), a combination of FLGs and ILGs located outward thereof (see absorbent article 100' shown in FIG. 5) and a combination of FLGs and ILGs located outward thereof and OLGs located further outward thereof (not shown) may be used.

The ILGs in absorbent article 100' are made by covering pieces of yarn-like rubber 30' that extend in the front-rear direction with right and left outer edge parts of top sheet 28' and they rise upwardly and inwardly from near the right and left outer edges of leak preventer 10'. These ILGs are not particularly limited and, for example, they may have a conventionally and publicly-known ILG configuration.

FLG 14' has head part 16', which has stretchability, and hanging part 18', which is configured by a non-woven fabric. In the crotch part, the lower end of this hanging part is coupled to the surface of top sheet 28' at fixing part 24' for the hanging part.

Leak preventer 10', absorber 12', FLG 14', head part 16', stretchable body M2, hanging part 18', front end coupling part 20', rear end coupling part 22', fixing part 24' for the hanging part and top sheet 28' in absorbent article 100', respectively correspond to leak preventer 11, absorber 13, FLG 15, head part 17, stretchable body M2, hanging part 19, front end coupling part 21, rear end coupling part 23, fixing part 25 for the hanging part and top sheet 28 in absorbent article 101, despite the fact that they differ with respect to details such as shape, etc.

Since absorbent article 100' is an underpants-type diaper, it does not have a detachable member. It has external covering sheet 31 that covers leak preventer 10' and forms an underpants shape and waist gather 35 that attaches closely around the waist of the wearer at the time of use.

In the present invention, the external covering sheet and waist gather are not particularly limited and, for example, any conventional and publicly-known external covering sheet and waist gather may be used.

The configuration of the FLG used in the absorbent article according to the present invention is not limited to the configurations of FLGs 14, 15 and 14'.

Hereinafter, the configuration of the FLG will be described in more detail.

The head part and the hanging part of the FLG may be integrally configured using one material. For example, the head part and the hanging part may be configured with the same stretchable material.

Alternatively, as with FLGs 14, 15 and 14', different materials may be used for the head part and the hanging part and then they may be integrally configured.

Hereinafter, the descriptions will be provided for the FLG in the order of (1) a head part, (2) a hanging part, (3) the integration and (4) the dimensions.

(1) Head Part (i) Shape and Arrangement

Shape examples of the head part include film-like, tape-like, band-like, tube-like and spiral coil-like shapes. Of these, a shape that can provide elasticity and cushioning properties when coupled with the material used in order to fit with the curved shape of the worn section of the wearer, is preferable.

The shape of the head part will be described in detail using the figures.

FIG. 6 contains schematic lateral end face views illustrating FLGs having head parts with various shapes. Each view shows the FLG on the left hand side when seen from the wearer. The FLG on the right hand side has a lateral end face view symmetric to the above, and in the present invention, the shapes of the right and left FLGs may be used interchangeably.

FLG 14a shown in FIG. 6(A) is configured by head part 16a and hanging part 18a. For the belt-like stretchable body used for head part 16a, for example, a stretchable film in sheet form, a rubber yarn composite band (for example, pajama rubber, manufactured by Fujihato, with a width of 15 mm and a rupture elongation of 210%), foam, and foam surrounded by a non-woven fabric may be used. Head part 16a has an advantage to the effect that it can be easily produced since it has a relatively simple configuration.

For the sheet-like member used for hanging part 18a, for example, an SMS non-woven fabric (for example, with a basis weight of 13 g/m$^2$) and a PE/PP spunbond non-woven fabric (for example, with a basis weight of 15 g/m$^2$) may be used such that their vertical length is, for example, 35 mm. The same applies to each of hanging parts 18'a to 18'd shown respectively in FIGS. 6(B) to 6(E) (the non-woven fabric in hanging part 18'd is to be used after being subjected to hydrophilization treatment).

The integration of head part 16a and hanging part 18a may be carried out through a method in which, for example, the belt-like stretchable body in an extended condition (for example, it may be extended twofold) is coupled to the sheet-like member through thermal fusion bonding. Thus, when an FLG is obtained by coupling the belt-like stretchable body, in an extended condition, which configures the head part, to the sheet-like member that configures the hanging part, as described with reference to FIG. 2, folds in pleated curtain form can be formed in the hanging part. As with the pleated curtain, the FLG according to this embodiment will have irregularities in the vertical direction at the lower end of the hanging part and also a thickness in the width direction in association with the formation of pleats.

FLG 14'*a* shown in FIG. 6(B) is configured by head part 16'*a* and hanging part 18'*a* and may be obtained by, for example, folding sheet-like stretchable body M3 in an inverted U-shape such that its inner side is positioned on the downward-facing side and by wrapping the body in such condition with an SMS non-woven fabric used for hanging part 18'*a*.

For sheet-like stretchable body M3, for example, a stretchable film and sheet-like foam (for example, polyurethane foam having a thickness of approximately 3 mm) may be used. Head part 16'*a* becomes bulky but excels in the cushioning properties and thus, there is an advantage of it being easy fitting with the wearer's skin.

FLG 14'*b* shown in FIG. 6(C) is configured by head part 16'*b* and hanging part 18'*b* and may be obtained by, for example, arranging belt-like stretchable body M4 made of two pieces of elastic yarn with a fine denier in the middle, arranging belt-like stretchable body M5 made of two pieces of elastic yarn with a coarse denier on both the right and left sides of the middle, and then by wrapping them with an SMS non-woven fabric used for hanging part 18'*b* and fixing them with a hot-melt adhesive. When this head part 16'*b* is extended in the front-rear direction at the time of use, a strong tension acts on the outside and it will assume a shape similar to a gutter facing upward and thus, an advantage is provided to the effect that it is relatively difficult for lateral shifting to Occur.

FLG 14'*c* shown in FIG. 6(D) is configured by head part 16'*c* and hanging part 18'*c* and may be obtained by, as opposed to the case of FLG 14'*b*, for example, arranging band-like stretchable body M5 made of two pieces of elastic yarn with a coarse denier in the middle, arranging belt-like stretchable body M4 made of two pieces of elastic yarn with a fine denier on both the right and left sides of the middle, and then by wrapping them with an SMS non-woven fabric used for hanging part 18'*c* and fixing them with a hot-melt adhesive. When this head part 16'*c* is extended in the front-rear direction at the time of use, a strong tension acts on the inside and it will assume a shape similar to an umbrella facing downward and thus, an advantage of being relatively easy fitting with the wearer's skin is provided.

FLG 14'*d* shown in FIG. 6(E) is configured by two types of head parts 17 and 16'*d* and two types of hanging parts 19 and 18'*d*. In FIG. 6(E), head part 17 and hanging part 19 on the left may be configured using FLG 15 shown in FIG. 4. In particular, they can be obtained by, for example, by arranging two polyurethane filaments as belt-like stretchable body M2 and then by surrounding them with a hydrophobic SMS non-woven fabric. In addition, in FIG. 6(E), head part 16'*d* and hanging part 18'*d* on the right may be obtained by, for example, using polyurethane foam, which excels in cushioning properties, as belt-like stretchable body M6 and by surrounding it with an SMS non-woven fabric which has been subjected to hydrophilization treatment with surfactant, and they are similar to the ones in FLG 14 shown in FIG. 2. By coupling of hanging parts 19 and 18'*d* such that the position of the top surface of head part 17 is slightly higher than the position of the top surface of head part 16', FLG 14' may be formed of head part 17 and hanging part 19 on the left and head part 16'*d* and hanging part 18'*d* on the right. Shifting the head part positions in this manner enables a closer fit to the wearer's skin and the transfer and leakage from the sides can be more effectively prevented.

FLG 14'*d* fulfills functions to the effect that the leakage from the side parts is suppressed by head part 17 and hanging part 19 located outward from the wearer (the left hand side in the figure) and that a bodily fluid, such as urine or the like, is collected by head part 16' and hanging part 18'*d* located inward to the wearer (the right hand side of the figure) so as to be diffused over the surface of the absorber.

As described above, FLG 14' is obtained by combining two types of FLGs and thus, the manufacturing process thereof is complex and costly. Accordingly, in the present invention, an FLG may be used in which only a part thereof, for example, a crotch part, has this double configuration.

The distance of the head part of the FLG from the surface of the absorber is not particularly limited, as long as it is within a range wherein the wearer's skin does not make contact with the absorber; however, it is defined by the length of the hanging part at the hanging part fixing part present in the crotch part and it is preferably 10 mm or more, or more preferably 15 mm or more, in the vicinity of the perineal area.

(ii) Materials

Since the head part of the FLG makes direct contact with the wearer's skin, the material used for the head part is preferably flexible and has both stretchability and cushioning properties, such as urethane expanded foam, and it is of particular importance for the material to have stretchability.

Examples of stretchable materials used for the head part will be provided below.

(a) Stretchable Materials Using a Filament-Like Elastic Body (Elastic Yarn)

In particular, for example, a so-called rubber band in tape form or tube form obtained by knitting and weaving elastic yarn such as rubber yarn, polyurethane filaments or the like; a stretchable knit fabric/woven fabric obtained by combined knitting/combined weaving elastic yarn and a synthetic filament such as a nylon filament, a polyester filament or the like; and a stretchable material which is associated with a deformation of construction such as a stretchable bandage, a tubular bandage, a stretchable supporter or the like, which is formed into net or tube form by using elastic yarn and spun yarn, may be provided.

Two or more of the above may be appropriately combined and used.

(b) Stretchable Films

In particular, for example, a synthetic resin film, such as a polyurethane film, an EVA (ethylene/vinyl acetate copolymer) film, an SEBS (styrene/ethylene/butylene/styrene copolymer) film, an SBR (styrene/butadiene rubber) film or the like; and a synthetic resin non-woven fabric, such as a polyurethane non-woven fabric or the like, may be provided. Among these stretchable films, those having stretchability only in one direction and those having stretchability in multiple directions are both usable.

Two or more of the above may be appropriately combined and used.

(c) Laminated Bodies of the Stretchable Materials in Sections (a) and (b) Above and Non-Woven Fabrics In particular, for example, a three-layered laminated body obtained by arranging a plurality of pieces of elastic yarn in a parallel manner and in an extended condition and by bonding non-woven fabrics from top and bottom; and a laminated body of an SEBS film and a non-woven fabric which is easily extendable in one direction, may be provided.

(2) Hanging Part (i) Shape and Arrangement

The shape of the hanging part will be described in detail using the figures.

FIG. 7 contains schematic partial side views illustrating FLGs having hanging parts with various shapes.

FLG 14*a* shown in FIG. 7(A) corresponds to the FLG shown in FIG. 6(A) and is configured by head part 16*a* and hanging part 18*a*. Head part 16*a* is also used in FLGs 14*b* to 14*f* illustrated in FIGS. 7(B) to 7(F).

Hanging part 18*a* of FLG 14*a* shown in FIG. 7(A) is configured in pleated curtain form by a sheet-like member without cut lines. This embodiment has high sealing properties with respect to bodily fluids and has a simple configuration which is easy to produce; however, since the stiffness is relatively high and deformation is difficult, it is necessary to select a thin and flexible material.

Hanging part 18*b* of FLG 14*b* shown in FIG. 7(B) is configured in a so-called "noren (i.e. shop-curtain) form" by a sheet-like member having a plurality of cut lines provided with a relatively wide interval therebetween. In this embodiment, when partitioning is made into three sections, for example, the middle part, front part and rear part, deformation may be facilitated by following the movement of the body.

Hanging part 18*c* of FLG 14*c* shown in FIG. 7(C) is configured in a so-called "tape form," in which a plurality of tapes hang down, by a sheet-like member having a plurality of cut lines provided with a relatively narrow interval therebetween. This embodiment facilitates deformation by even more following the movement of the body; however, the production thereof may become slightly difficult and the sealing properties with respect to bodily fluids may be somewhat compromised.

Hanging part 18*d* of FLG 14*d* shown in FIG. 7(D) is configured as a combination of the so-called "tape forms" and "noren forms" by a sheet-like member having a plurality of cut lines provided with a relatively narrow interval therebetween in the front body and the rear body and having no cut lines in the crotch part. This embodiment has a configuration that takes advantage of the beneficial feature of FLG 14*c* and that can make up for the defects thereof and thus, is easily producible and also excels in sealing properties with respect to bodily fluids.

In hanging parts 18*a* to 18*d* shown in FIGS. 7(A) to 7(D), the cut lines provided in the sheet-like member are relatively deep, reaching substantially as far as head part 16*a*. However, in the present invention, they may be a shallow cut line, remaining at the end of the hanging part, and a cut line that extends up to near the middle of the hanging part and so on, and an appropriate combination thereof may also be used.

Alternatively, instead of a cut line, a cutout having a certain width may also be used.

When the sheet-like member has cut lines, an advantage to the effect that folds, kinks or the like are less likely to occur in the absorber is provided due to a higher degree of freedom of the hanging part. On the other hand, the effect of blocking, at the side faces, the bodily fluid that flows over the surface of the absorber from the side parts, is somewhat weakened.

Accordingly, it is important to appropriately select the number, position and depth of the cut lines and the manner of mixing cut lines which have different depths, in consideration of the position of the hanging part, the properties (for example, stiffness) of the material for the sheet-like member used for the hanging part or the like.

Hanging part 18*e* of FLG 14*e* shown in FIG. 7(E) is configured by a plurality of tufts made of a plurality of fine pieces of yarn hanging down from head part 16*a*. This embodiment is extremely easily fittable by following the movement of the body and has an effect wherein the bodily fluid separated by the head part is distributed and evenly provided to the absorber; however, the sealing properties with respect to bodily fluids are somewhat compromised.

Hanging part 18*f* of FLG 14*f* shown in FIG. 7(F) is configured in a so-called "grid form" by a sheet-like member provided with a plurality of fine pores. This embodiment excels in deformability to a certain degree and also in sealing properties with respect to bodily fluids; however, it is necessary to select a special material.

The arrangement of an FLG in the absorbent article is not particularly limited, and the hanging part may hang down from the inner side (the middle side) with respect to the head part, as shown in FIG. 4(B), or the hanging part may hang down from the middle of the head part or the hanging part may hang down from the outer side (the side edge side) with respect to the head part, as shown in FIG. 2(B) and FIGS. 6(A) to 6(E).

(ii) Materials

Examples of materials used for the hanging part include fabric foils, films, nets and non-woven fabrics. Of these, when the cost, workability and the like are considered, non-woven fabrics produced in a wet-type, dry-type, spunlace, spunmelt, etc. approach are preferable, and a spunmelt non-woven fabric such as an SMS, SMMS, etc. is more preferable.

The spunmelt non-woven fabric is a spunbonded or spunbonded/meltblown laminated body having a polymer configuration of PE, PP, PET, PE/PP, PE/PET or the like. The spunmelt non-woven fabric having a basis weight of 10-20 g/m² is preferable in terms of the cost, workability and the like.

(3) Integration

When different materials are used for the head part and the hanging part, they may be integrated to form the FLG.

As an example embodiment of the integration, as in FLGs 14 and 15 described above, the embodiment in which the stretchable body is enwrapped by the sheet-like member and the overlapping parts of the sheet-like member are coupled may be provided. This embodiment has an advantage to the effect that the integration of the head part and the hanging part becomes strong.

In addition, as with FLG 14*a* shown in FIG. 6(A), an embodiment in which the stretchable member and the sheet-like member are simply coupled and integrated with each other, may also be provided.

The coupling means used when integrating the head part and the hanging part is not particularly limited, and examples thereof include sewing using a sewing machine, thermal sealing, ultrasonic sealing and hot-melt bonding. Two or more of the above may be combined and used.

When a stretchable body is used for the material of the head part, it is preferable for the integration to be performed under extension.

(4) Dimensions (i) Width

The head part of an FLG may have various shapes; however, in general, the width (the length in the lateral direction) thereof is preferably 2 mm or more, and more preferably 5 mm or more, in terms of avoiding pain even when it makes contact with and presses against the wearer's skin at the time of use, as well as in terms of leaving no marks. The width of the head part is preferably 50 mm or less in terms of easy handling at the time of use and avoiding high cost.

(ii) Length in the Vertical Direction

Most of the length in the vertical direction of an FLG is occupied by the hanging part.

The length in the vertical direction of the hanging part is preferably 10 mm or more, and more preferably 20 mm or more, in terms of excelling in the effect of blocking, at the side faces, the bodily fluid that flows over the absorber surface from the side part; however, this may vary depending on the distance between the head part and the absorber surface. The length in the vertical direction of the hanging part is not particularly limited, and it may be in a condition in contact with the absorber surface; however, it is preferably 50 mm or less in terms of avoiding high cost.

Effects achievable by an FLG will be described below.

An FLG basically makes contact with the wearer's skin in a condition where it is spaced from the absorber surface and floating therefrom and thus, the direct contact of the wearer's skin with the bodily fluid absorbed in the absorber or the bodily fluid present over the absorber, is effectively prevented and skin troubles, such as diaper rash or the like, can be extremely effectively suppressed.

Further, the following effects may be provided as secondary effects.

An FLG is basically spaced from the absorber surface and floating therefrom and thus, it would not receive any impact from the stiffness of the absorber and it would be difficult for folds, kinks or the like to occur in the absorber. Namely, since the head part of the FLG, which supports the hanging part of the FLG and retains the structure, is present at a position significantly separated from the absorber surface, even when the hanging part is fixed to the absorber at the hanging part fixing part, the movements of the FLG and absorber are not constrained by each other.

Accordingly, the folds, kinks or the like are unlikely to occur in the absorber at the time of use of the absorbent article and the absorption capability of the absorber can be sufficiently fulfilled.

In addition, when the wearer puts on the absorbent article, the position for the FLG presence optimal for the shape of the wearer's body can be selected without considering the positional relationship with respect to the absorber. This will suppress the feeling of discomfort of the wearer at the time of use.

Moreover, since the head part of the FLG and the wearer's skin can be kept in a constantly adhered condition to each other, the head part can be made to flexibly follow the movement of the wearer's body and thus, transfer and leakage from the side parts, which are prone to occur due to the movement of the wearer's body, can be suppressed.

Furthermore, since the FLG is basically spaced apart from the absorber surface, it is not necessary to design it integrally with the absorber. Namely, by providing an FLG in the absorbent article, the degree of freedom for designing the absorber can be increased.

Table 1 describes and compares the difference between the FLG and the conventional ILG for each configuration.

TABLE 1

| Comparison points | ILG (conventional art) | FLG according to the invention |
|---|---|---|
| Gather configuration | Configured from belt-like head part and sheet-like leg part | Configured from belt-like head part and sheet-like hanging part |
| Bonding to the absorbent article body Front end part and rear end part Front body Crotch part Rear body | Both head part and leg part are bonded and fixed to body end parts Base end part of leg part is fixed to absorber surface Base end part of leg part is fixed to absorber surface Base end part of leg part is fixed to absorber surface | Both head part and hanging part are bonded and fixed to body end parts Hanging part is not fixed and is in a floating condition Lower end of hanging part is partially fixed to absorber surface Hanging part is not fixed and is in a floating condition |
| Gather base end part (support point) | Gather rises using absorber surface as base end part | Hanging part hangs down from floating head part |
| Interval between head parts in width direction of absorbent article | Corresponds to the entire absorber width | Preferably equal to or smaller than the width of perineal area in crotch part |
| Leg part rising position/Hanging part hanging down position | Both sides of absorber | Near the middle in crotch part |
| Arrangement condition of a pair of right and left gathers above absorber | Generally, arrangement is made such that head part is inside and leg part is outside, and head parts are opposed to each other | Preferably, arrangement is made such that head part is outside and hanging part is inside, and hanging parts are opposed to each other |
| Worn condition with respect to narrow crotch part at the time of use | Absorber is deformed as if it is being folded and is inserted with ILG | Absorber remains at a spaced position and floating head part of FLG adheres to wearer's skin (perineal area or the like) |

Subsequently, the arrangement of an FLG in the absorbent article according to the present invention will be described in more detail.

FIG. 8 is a schematic plan view of absorbent article 100 according to the present invention. In FIG. 8, the details of the respective members are omitted and only the outer circumference edge of absorbent article 100 is shown by approximating it to a rectangle having a concave portion in the middle part in the length direction (detachable members 26 are omitted).

The terms used for describing the arrangement of the FLGs from FIG. 9 will be defined using FIG. 8.

In general, an absorbent article is symmetrical in a plan view. Absorbent article 100 is also symmetrical in FIG. 8, which is a plan view, and thus, a symmetry axis (corresponding to the line which is drawn in the middle in the width direction) will be denoted by vertical center line CL-a.

Then, the line drawn at the position in the middle between the front end edge and the rear end edge in the length direction of absorbent article 100 is denoted by lateral center line CL-b. The area around lateral center line CL-b is denoted by crotch part C, the area in front of crotch part C is denoted by front body F and the area to the rear thereof is denoted by rear body R. It should be noted that, at the time of use of the absorbent article, the perineum of the wearer's crotch part will be located slightly forward of lateral center line CL-b (in the case of an infant's diaper, it will be located at approximately 20 mm forward thereof).

FIG. 9 contains schematic plan views of the absorbent articles with FLGs in various arrangement embodiments. It should be noted that, in FIG. 9, the details of the respective members are omitted except for the FLGs. Further, in the examples, the head parts of the FLGs are partially present, rather than over the entire length of the FLGs; however, the head parts of the FLGs may be present over the entire length of the FLGs.

In absorbent article 102 shown in FIG. 9(A), a pair of right and left FLGs 15a are arranged such that, while sandwiching vertical center line CL-a therebetween, both head parts 17a face outward and both hanging parts 19a face inward, and such that the lower end parts of hanging parts 19a are opposed to each other near the middle in the width direction of the absorber (not shown). In this way, a form is obtained in which the right and left width intervals are easily adjusted.

In addition, the lower end parts of the pair of hanging parts 19a are arranged substantially in a parallel manner over the entire length in the length direction. This embodiment has a simple configuration and the production process can be simplified.

In the vicinity of lateral center line CL-b in crotch part C, hanging parts 19a are fixed to the absorber (not shown) at hanging part fixing parts 25a.

In absorbent article 103 shown in FIG. 9(B), as with absorbent article 102, a pair of right and left FLGs 15b are arranged such that, while sandwiching vertical center line CL-a therebetween, both head parts 17b face outward and both hanging parts 19b face inward, and such that the lower end parts of hanging parts 19b are opposed to each other near the middle in the width direction of the absorber (not shown).

In addition, the spaced-apart distance between the pair of hanging parts 19b is arranged such that it is narrow in the crotch part and widens from crotch part C toward each of front body F and rear body R. This embodiment has a configuration that allows fitting to the perineal area and that, at the same time, covers a wide area of the abdominal region and dorsal region, and thus, a form that facilitates wearing is obtained.

In the vicinity of lateral center line CL-b in crotch part C, hanging parts 19b are fixed to the absorber (not shown) at hanging part fixing parts 25b.

In absorbent article 104 shown in FIG. 9(C), as with absorbent article 102, a pair of right and left FLGs 15c are arranged such that, while sandwiching vertical center line CL-a therebetween, both head parts 17c face outward and both hanging parts 19c face inward, and such that the lower end parts of hanging parts 19c are opposed to each other near the middle in the width direction of the absorber (not shown).

In addition, the spaced-apart distance between the pair of hanging parts 19c is arranged such that it narrows down from crotch part C to rear body R and widens from crotch part C toward front body F. This embodiment has a form in which the feces are unlikely to spread to the sides when they are excreted.

In the vicinity of lateral center line CL-b in crotch part C, hanging parts 19c are fixed to the absorber (not shown) at hanging part fixing parts 25c.

In absorbent article 105 shown in FIG. 9(D), as with absorbent article 102, a pair of right and left FLGs 15d are arranged such that, while sandwiching vertical center line CL-a therebetween, both head parts 17d face outward and both hanging parts 19d face inward, and such that the lower end parts of hanging parts 19d are opposed to each other near the middle in the width direction of the absorber (not shown).

In addition, the spaced-apart distance between the pair of hanging parts 19d is arranged such that it narrows down from crotch part C to front body F and widens from crotch part C toward rear body R. This embodiment has a form in which the seeping out from the front part is prevented when urine is excreted.

In the vicinity of lateral center line CL-b in crotch part C, hanging parts 19d are fixed to the absorber (not shown) at hanging part fixing parts 25d.

In absorbent article 106 shown in FIG. 9(E), as with absorbent article 102, a pair of right and left FLGs 15e are arranged such that, while sandwiching vertical center line CL-a therebetween, both head parts 17e face outward and both hanging parts 19e face inward, and such that the lower end parts of hanging parts 19e are opposed to each other near the middle in the width direction of the absorber (not shown).

In addition, the spaced-apart distance between the pair of hanging parts 19e is, as with absorbent article 105, arranged such that it narrows down from crotch part C to front body F and widens from crotch part C toward rear body R; however, in the vicinity of the front end edge of front body F of absorbent article 106, the pair of FLGs 15e are provided such that they overlap with each other. In this embodiment, the overlapping sections form a pocket in the front end part of absorbent article 106 at the time of use and this pocket serves to prevent the bodily fluid from leaking out from the front end of absorbent article 106 by flowing over the surface of the absorber (not shown) when the wearer assumes a face-down position.

In the vicinity of lateral center line CL-b in crotch part C, hanging parts 19e are fixed to the absorber (not shown) at hanging part fixing parts 25e.

In absorbent article 107 shown in FIG. 9(F), as with absorbent article 102, a pair of right and left FLGs 15f are arranged such that, while sandwiching vertical center line CL-a therebetween, both head parts 17f face outward and both hanging parts 19f face inward, and such that the lower end parts of hanging parts 19f are opposed to each other near the middle in the width direction of the absorber (not shown); however, it differs therefrom with respect to the point that the length in the vertical direction of hanging parts 19f at crotch part C is large and such length in front body F and back body R is small, as well as the point that parts of hanging parts 19f are arranged so as to overlap with each other in crotch part C. This embodiment has advantages to the effect that it has a form in which the bodily fluid can be easily collected and guided to the crotch part and that, at the same time, only one hanging part fixing part is necessary.

In the vicinity of lateral center line CL-b in crotch part C, the overlapping parts of hanging parts 19f are fixed to the absorber (not shown) at one fixing part 25f for the hanging part.

In absorbent article 108 shown in FIG. 9(G), as with absorbent article 102, a pair of right and left FLGs 15g are arranged such that, while sandwiching vertical center line CL-a therebetween, both head parts 17g face outward and both hanging parts 19g face inward, and such that the lower end parts of hanging parts 19g are opposed to each other near the middle in the width direction of the absorber (not shown); however, it differs therefrom with respect to the point that the length in the vertical direction of hanging parts 19g is large only at a portion of crotch part C and parts of hanging parts 19g are arranged such that they overlap with each other at this portion of crotch part C. Although this embodiment differs, in form, from FLG 15f, they share common advantages to the effect that the bodily fluid can be easily collected and guided to the crotch part and that, at the same time, only one hanging part fixing part is necessary.

In the vicinity of lateral center line CL-b in crotch part C, the overlapping parts of hanging parts 19g are fixed to the absorber (not shown) at one fixing part 25g for the hanging part.

FIG. 10 contains schematic plan views of the absorbent articles with FLGs in various arrangement embodiments. It should be noted that, in FIG. 10, the details of the respective members are omitted except for the FLGs and the coupling band.

In absorbent article 109 shown in FIG. 10(A), a pair of right and left FLGs 15h are arranged such that, while sandwiching vertical center line CL-a therebetween, both head parts 17h face outward and both hanging parts 19h face inward, and such that the lower end parts of hanging parts 19h are relatively spaced apart and opposed to each other.

The pair of hanging parts 19h are coupled to each other by coupling band 32 in the vicinity of lateral center line CL-b of crotch part C. Coupling band 32 couples to the surface of the absorber (not shown) at coupling band fixing part 34 located in the middle of coupling band 32. Hanging parts 19h of FLGs 15h are not fixed to the absorber (not shown) in front body F and rear body R; however, they are indirectly fixed to the absorber (not shown) via coupling band 32 in the crotch part.

Accordingly, the embodiment in which the hanging parts of the FLGs are indirectly fixed to the absorber via the coupling band has an advantage to the effect that, even when the spaced-apart distance between the pair of hanging parts is relatively large, the hanging parts can be made to couple to the absorber without applying unnecessary stress to the FLGs. In addition, the length of the hanging parts can also be made small, resulting in another advantage wherein the amount of material used for the hanging parts can be reduced.

It should be noted that, in the present invention, in the case where the surface of the absorber is covered with a top sheet, an embodiment in which the coupling band coupled to the hanging parts of the FLGs is fixed to the top sheet is also included in the embodiments in which the hanging parts of the FLGs are fixed to the absorber, since such hanging parts are indirectly fixed to the absorber via the coupling band and the top sheet.

Coupling band 32 is in a tape form having a length in the front-rear direction of 10 mm and a width in the lateral direction of 50 mm. The shape and dimensions of the coupling band are, however, not particularly limited. The coupling band is preferably in a stripe form or a tape form (neither being limited to a rectangular shape). In such case, the width thereof is preferably 20-60 mm and the length thereof is 10-100 mm.

The material for the coupling band is not particularly limited, and it may be the same as or different from the material used for the hanging parts.

As shown in FIG. 10(A), the under surface of coupling band 32 couples to the inner (top) surfaces of the pair of hanging parts 19h at coupling parts 36. This embodiment has a great effect of holding and fixing the right and left hanging parts over the entire width of the coupling band.

Coupling parts 36 at which coupling band 32 couples to hanging parts 19h are located near the lower end parts of hanging parts 19h.

The method of coupling between the coupling band and the absorber or the top sheet covering the absorber, and the method of coupling between the coupling band and the hanging parts, will be described below.

Absorbent article 110 shown in FIG. 10(B) is basically similar to absorbent article 109; however, the method of coupling between coupling band 32 and hanging parts 19h is different. Namely, in absorbent article 110, the top surface of coupling band 32 couples to the outer (under) surfaces of the pair of hanging parts 19h at coupling parts 36a. Due to the fact that merely sealing points are present, the fixing effect of the right and left hanging parts in this embodiment is relatively weak as compared to the embodiment shown in FIG. 10(A); however, the production process thereof is simplified.

Absorbent article 111 shown in FIG. 10(C) is basically similar to absorbent article 109; however, the shape of coupling band 33 is different. Namely, coupling band 33 used in absorbent article 111 is in a stripe shape having a length in the front-rear direction of 40 mm and a width in the lateral direction of 50 mm.

Coupling band 33 and the absorber (not shown) are coupled to each other at coupling band fixing part 34a, which is in a spot form and located substantially in the middle in the length direction and also in the middle in the width direction of coupling band 33, and the forward part and the rearward part of coupling band 33 are not coupled to the absorber (not shown).

In addition, coupling band 33 and hanging parts 19h are coupled to each other at coupling parts 36b, extending in the length direction on both the right and left side edges of coupling band 33.

In this embodiment, at the time of use, coupling band 33 rises, in front of and to the rear of coupling band fixing part 34a in crotch part C, with FLGs 15h and forms pockets in front of and to the rear of crotch part C. Thus, the mixing of urine excreted in front of crotch part C and feces excreted to the rear of crotch part C is effectively prevented and the occurrence of odors and rashes can be suppressed. Additionally, an effect of effectively capturing urine and feces can also be achieved.

Absorbent article 112 shown in FIG. 10(D) is basically similar to absorbent article 111; however, the position of coupling band 33 is different.

Coupling band 33 and the absorber (not shown) are coupled to each other at coupling band fixing part 34b, which is in a spot form and located at the rear part in the length direction and in the middle of the width direction of coupling band 33, and the forward part of coupling band 33 is not coupled to the absorber (not shown).

In addition, coupling band 33 and hanging parts 19h are coupled to each other at coupling parts 36c, extending in the length direction on both the right and left side edges of coupling band 33.

In this embodiment, at the time of use, coupling band 33 rises, in front of coupling band fixing part 34b in crotch part C, with FLGs 15h and forms a pocket in front of crotch part C. Thus, the mixing of urine excreted in front of crotch part C and feces excreted to the rear of crotch part C is effectively prevented and the occurrence of odors and rashes can be suppressed. Additionally, an effect of effectively capturing urine can also be achieved.

Absorbent article 113 shown in FIG. 10(E) is basically similar to absorbent article 111; however, the position of coupling band 33 is different.

Coupling band 33 and the absorber (not shown) are coupled to each other at coupling band fixing part 34c, which is in a spot form and located at the front part in the length direction and in the middle in the width direction of coupling band 33, and the rearward part of coupling band 33 is not coupled to the absorber (not shown).

In addition, coupling band 33 and hanging parts 19h are coupled to each other at coupling parts 36d, extending in the length direction on both the right and left side edges of coupling band 33.

In this embodiment, at the time of use, coupling band 33 rises, to the rear of coupling band fixing part 34c in crotch part C, with FLGs 15h and forms a pocket to the rear of crotch part C. Thus, the mixing of urine excreted in front of crotch part C and feces excreted to the rear of crotch part C is effectively prevented and the occurrence of odors and rashes can be suppressed. Additionally, an effect of effectively capturing feces can also be achieved.

The fixing condition between the hanging parts of the FLG and the absorber will now be described in more detail.

FIG. 11 contains views for describing the fixing condition between the hanging parts of the FLGs and the absorber. All of FIGS. 11(A) to 11(D) are plan views, and only FLGs, a coupling band and a top sheet are shown therein as components; however, an absorber (or a top sheet covering the absorber) is present on the underside (the deep side when seen from the plane of the drawing) of the hanging part fixing part and coupling part fixing part.

FLG 38 shown in FIG. 11(A) is configured from head part 40 and hanging part 42, and, as with the various FLGs shown in FIGS. 1, 3 and 9(A) to 9(E), the lower end parts of hanging parts 42 are arranged such that, while sandwiching vertical center line CL-a therebetween, they are spaced apart and opposed to each other near the middle in the width direction of the absorber.

Although it may depend on the length of the hanging parts, the minimum spaced-apart distance La between the pair of hanging parts is preferably 40 mm or less and more preferably 30 mm or less. Within this range, the positional displacement in the width direction may be suppressed and it becomes easy to stably locate head parts 40, in the crotch part, at the perineum.

It should be noted that it is possible to set the minimum spaced-apart distance between the pair of hanging parts as 0 mm, or alternatively, portions thereof may be overlapped with each other.

In addition, the minimum spaced-apart distance between the pair of head parts is not particularly limited; however, in order to allow the head parts to be more stably located, in the crotch part, at the perineum, such distance is preferably equal to or smaller than the width of the perineum. In particular, when it is assumed that the absorbent article according to the present invention is an absorbent article for infants, it is preferable for the minimum separated-apart distance between the pair of head parts to be set to 30-50 mm in a floating condition.

In FLG 38 shown in FIG. 11(A), fixing part 44 for the hanging part that fixes hanging part 42 and the absorber (not shown) to each other is located at a position 5-10 mm outward from the lower end of the hanging part and is provided in a linear form having a length in the length direction of 20-30 mm.

It should be noted that, when the absorber is covered by a top sheet, the hanging part is fixed to the top sheet and is indirectly coupled to the absorber via the top sheet.

FLG 38a shown in FIG. 11(B) is configured from head part 40a and hanging part 42a, and, as with the various FLGs shown in FIGS. 9(F) and 9(G), is arranged such that parts of hanging parts 40a overlap with each other in the crotch part.

The overlapping parts of the pair of hanging parts are fixed to the absorber (not shown) at fixing part 44a for the hanging part, which is provided linearly on vertical center line CL-a.

Accordingly, when the overlapping parts of the pair of hanging parts are only fixed on the vertical center line CL-a, width Lb in the lateral direction of the overlapping parts of the hanging parts is preferably 40 mm or less, and more preferably 30 mm or less. Within this range, there is no "play" part at the lower end parts of the hanging parts and thus, a stable condition can be obtained.

In FLG 38a, the coupling between the pair of hanging parts 42a is also performed at inter-hanging part coupling part 46.

During production of the absorbent article according to the present invention, the fixing of hanging parts 42a to the absorber (not shown) at fixing part 44a for the hanging part and the coupling between the pair of hanging parts 42a at inter-hanging part coupling part 46, may be performed simultaneously or separately.

It should be noted that, when the absorber is covered with a top sheet, the hanging part is fixed to the top sheet and is indirectly coupled to the absorber via the top sheet.

FLG 38b shown in FIG. 11(C) is configured from head part 40b and hanging part 42b, and, as with FLG 38a shown in FIG. 11(B), parts of hanging parts 42b are arranged such that they overlap with each other in the crotch part; however, as compared to the case of FLG 38a, the overlapping parts of the pair of hanging parts in this case are larger.

The overlapping parts of the pair of hanging parts are fixed to top sheet 48 at hanging part fixing parts 44b, which are provided linearly in the vicinity of the lower end parts of the pair of hanging parts and are fixed to the absorber (not shown) via top sheet 48. Fixing part 44b for the hanging part is configured by dots arrayed in the length direction.

Accordingly, when the overlapping parts of the pair of hanging parts are fixed to the absorber via the top sheet at a plurality of locations, width Lc in the lateral direction of the overlapping parts of the hanging parts can be made wider, as compared to the case in which the fixing is made at one location, as in FLG 38a. Width Lc in the lateral direction of the overlapping parts of the hanging parts is not particularly limited; however, such length is preferably 80 mm or less, and more preferably 60 mm or less, in view of the loss of material and the like. Further, in order to strengthen the fixing between the hanging part fixing part and the top sheet or the absorber, such width is preferably 40 mm or more.

In FLG 38b, the coupling between the pair of hanging parts 42b is also performed at inter-hanging part coupling part 46a. Inter-hanging part coupling part 46b is configured by dots arrayed in the length direction.

During production of the absorbent article according to the present invention, the fixing of hanging parts 42b to top sheet 48 at hanging part fixing parts 44b and the coupling between the pair of hanging parts 42b at inter-hanging part coupling part 46a, may be performed simultaneously or separately.

It should be noted that, when the absorber is not covered with the top sheet, the hanging parts are directly coupled to the absorber.

FLG 38c shown in FIG. 11(D) is configured from head part 40c and hanging part 42c, and, as with the various FLGs shown in FIGS. 10(A) to 10(E), hanging parts 42c are arranged such that they are relatively spaced apart and are opposed to each other, and a pair of hanging parts 42c are coupled to each other by coupling band 50. Coupling band 50 is coupled to the surface of the absorber (not shown) at coupling band fixing part 52, which is in a spot form and located in the middle of coupling band 50 and on vertical center line CL-a. The coupling between hanging parts 42c and coupling band 50 is performed at coupling parts 54, extending in the length direction in the vicinity of the lower end parts of the hanging parts.

The fixing of the hanging parts of the FLGs to the absorber or the top sheet, the coupling between the pair of hanging parts, the fixing of the coupling band to the absorber or the top sheet, and the coupling between the coupling band and the hanging parts, are all not particularly limited and are as described below.

Examples of means for fixing and coupling include thermal heating, ultrasonic sealing and making use of adhesives such as a hot-melt adhesive, and so on.

Examples of fixing and coupling patterns include a line form, a dot form and a hatching form.

The dimensions of fixing and coupling locations are not particularly limited, and, in the case of a line form, the line width is preferably 1-3 mm and the line length is preferably 10-50 mm.

The number of fixing and coupling locations may be one or, alternatively, more than one.

Next, the fixing condition when arranging an FLG to the absorbent article body will now be described.

FIG. 12 contains views for describing the fixing condition when arranging an FLG to the absorbent article body.

All of FIGS. 12(A) to 12(C) are plan views, and only the FLGs extending from the front body to the crotch part are shown therein, in addition to the absorbent article body, as components.

In the absorbent article body, in general, no absorber is present at its front end part, and the absorbent article has a configuration in which a top sheet is exposed when such top sheet is provided or a leak preventer is exposed when such top sheet is not provided.

In absorbent article 114 shown in FIG. 12(A), FLG 38d, having head part 40d and hanging part 42d, is arranged. FLG 38d is one example that, in the vicinity of the front end part of FLG 38d, no member configures head part 40d is present, and FLG 38d is only formed with a sheet-like member that configures hanging part 42d.

The sheet-like member that forms FLG 38d is coupled to the body (the leak preventer or top sheet) of absorbent article 114, in its substantially entire width direction, at front end coupling part 20a. Length $S_1$ in the length direction of front end coupling part 20a is preferably in the range of 10-80 mm.

Absorbent article 115 shown in FIG. 12(B) has FLG 38d, as with absorbent article 114; however, the coupling condition with respect to the body of absorbent article 115 is different.

The sheet-like member that forms FLG 38d is coupled to the body (the leak preventer or top sheet) of absorbent article 115, at front end coupling part 20b, by way of two locations, i.e. inner and outer locations, in the width direction of the sheet-like member. Length $S_2$ in the length direction of front end coupling part 20b, i.e. the two locations, is preferably in the range of 20-80 mm. Width $R_1$ and width $R_2$ of front end coupling part 20b, i.e. the two locations, are preferably in the range of 2-15 mm.

As with absorbent article 115, in absorbent article 116 shown in FIG. 12(C), the sheet-like member that forms FLG 38d is coupled to the body (the leak preventer or top sheet) of absorbent article 116, at front end coupling part 20c, by way of two locations, i.e. inner and outer locations, in the width direction of the sheet-like member. However, absorbent article 116 differs therefrom with respect to the point that the length in the length direction is different for front end coupling part 20c, i.e. for each of the two locations. Namely, length $S_3$ in the length direction of the outer front end coupling part 20c is longer than length $S_4$ in the length direction of the inner front end coupling part 20c. In the present invention, as opposed to this, the length in the length direction of the outer front end coupling part may also be shorter than the length in the length direction of the inner front end coupling part.

The fixing near the rear end part of the absorbent article body can be performed in a similar manner to the fixing near the front end part of the absorber article body as described above.

When the head part of the FLG has stretchability, the coupling between the front end part and rear end part of the hanging part of the FLG and the vicinity of the front end part and rear end part of the absorbent article body is preferably performed in a condition in which the FLG is stretched in the front-rear direction. In this way, the configuration in which the FLG is floating can easily be achieved.

According to the present invention, members other than the FLG, for example, a pocket formed by a leak-preventive material or an elastic fabric for forming an elastic ring around the waist, may further be provided to the front end part and rear end part of the absorbent article body.

In addition to the various members described above, the absorbent article according to the present invention may further be provided with, for example, various constituent members of the conventionally and publicly-known absorbent articles.

The absorbent article according to the present invention may be in the form of a waist band type or underpants type (i.e. tapeless type).

As described above, the absorbent article according to the present invention is illustrated based on the respective embodiments illustrated herein; however, it should be noted that the present invention is not limited to these embodiments and, for example, the configurations of the respective parts may be replaced with any configuration capable of performing a similar function.

In addition, the configurations of the respective parts in the respective embodiments may be combined in an arbitrary manner to obtain other embodiments.

The absorbent article according to the present invention may be preferably used for disposable diapers (for infants and adults), incontinence articles, training pants, diaper covers which can be used multiple times by washing, or the like.

DESCRIPTION OF THE REFERENCE NUMERALS 10, 10', 11 Leak preventer
12, 12', 13 Absorber
14, 14', 14a, 14b, 14c, 14d, 14e, 14f, 14'a, 14'b, 14'c, 14'd, 15, 15a, 15b, 15c, 15d, 15e, 15f, 15g, 15h, 38, 38a, 38b, 38c, 38d Floating leg gather (FLG)
16, 16', 16a, 16'a, 16'b, 16'c, 16'd, 17, 17a, 17b, 17c, 17d, 17e, 17f, 17g, 17h, 40, 40a, 40b, 40c, 40d Head part
18, 18', 18a, 18b, 18c, 18d, 18e, 18f, 18'a, 18'b, 18'c, 18'd, 19, 19a, 19b, 19c, 19d, 19e, 19f, 19g, 19h, 42, 42a, 42b, 42c, 42d Hanging part
20, 20', 20a, 20b, 20c, 21 Front end coupling part
22, 22', 23 Rear end coupling part
24, 24', 24a, 25, 25a, 25b, 25c, 25d, 25e, 25f, 25g, 44, 44a, 44b Fixing part for the hanging part
26, 27 Detachable member
28, 48 Top sheet
30, 30' Yarn-like rubber
31 External covering sheet
32, 33, 50 Coupling band
34, 34a, 34b, 34c, 52 Coupling band fixing part
35 Waist gather
36, 36a, 36b, 36c, 36d, 54 Coupling part
46, 46a Inter-hanging part coupling part
100, 101, 102, 103, 104, 105, 106, 107, 108, 109, 110, 111, 112, 113, 114, 115, 116 Absorbent article
C Crotch part
CL-a Vertical center line
CL-b Lateral center line
F Front body
M1, M2, M3, M4, M5, M6 Stretchable body
R Rear body

The invention claimed is:
1. An absorbent article, comprising:
a leak preventer in sheet form;
an absorber that is arranged above the leak preventer and is capable of absorbing a bodily fluid in at least one layer; and
a pair of floating leg gathers, comprising a right floating leg gather and a left floating leg gather, that are arranged, above the absorber, from a front end part to a rear end part in a length direction of a body of the absorbent article via a front body, a crotch part and a rear body,
wherein the floating leg gathers have head parts and hanging parts that connect to the head parts, respectively, a front end part and a rear end part of each of the hanging parts respectively being coupled near to a front end part and near to a rear end part of the body of the absorbent article, and each of the hanging parts hangs down from the head part toward the absorber,
wherein the hanging parts of the floating leg gathers are directly or indirectly fixed to the absorber at a lower end part of the hanging part in the crotch part, without fixing to the absorber in the front body and the rear body,
wherein, at a time of use, the head parts of the floating leg gathers make contact with a wearer's skin and maintain a spaced-apart condition with respect to the absorber, and
wherein each of the head parts of the pair of floating leg gathers is positioned outwardly from the respective hanging part, relative to a longitudinal centerline of the absorbent article, and the lower end parts of the pair of hanging parts are opposed to each other near the longitudinal cernterline in a width direction of the absorber.

2. The absorbent article according to claim 1, wherein a spaced-apart distance between the pair of hanging parts is narrow at the crotch part and widens from the crotch part toward each of the front end part and the rear end part.

3. The absorbent article according to claim 1, wherein a spaced-apart distance between the pair of hanging parts narrows down from the crotch part to the rear end part and widens from the crotch part toward the front end part.

4. The absorbent article according to claim 1, wherein a spaced-apart distance between the pair of hanging parts narrows down from the crotch part to the front end part and widens from the crotch part toward the rear end part.

5. The absorbent article according to claim 1, wherein the minimum spaced-apart distance between the lower end parts of the hanging parts of the pair of floating leg gathers is 40 mm or less.

6. The absorbent article according to claim 1, wherein parts of the pair of hanging parts overlap with each other in the crotch part.

7. The absorbent article according to claim 1, wherein further comprising a coupling band that couples the hanging parts of the pair of floating leg gathers to each other at the crotch part, and
by the coupling band being fixed to the absorber at the crotch part, the hanging parts of the floating leg gathers are indirectly fixed to the absorber.

8. The absorbent article according to claim 1, wherein each of the hanging parts of the floating leg gathers is directly or indirectly fixed to the absorber at a plurality of locations in the crotch part.

9. The absorbent article according to claim 1, wherein the hanging parts of the floating leg gathers each have a cut line or a cutout.

10. The absorbent article according to claim 1, wherein the head parts of the floating leg gathers each have stretchability.

11. The absorbent article according to claim 10, wherein each of the floating leg gathers is formed by coupling a belt-like stretchable body to a sheet-like member in an extended condition, the belt-like stretchable body configuring the head part, the sheet-like member configuring the hanging part, and
the hanging part has folds.

12. The absorbent article according to claim 10, wherein the coupling is respectively performed between the front end part and the rear end part of the hanging part of each of the floating leg gathers and near the front end part and near the rear end part of the body of the absorbent article, in a condition in which the floating leg gathers are stretched in a front-rear direction.

13. The absorbent article according to claim 1, further comprising right and left inner leg gathers respectively provided further outside from the positions where the floating leg gathers are present in the width direction.

14. The absorbent article according to claim 1, further comprising right and left outer leg gathers respectively provided further outside from the positions where the floating leg gathers are present in the width direction.

* * * * *